US006979290B2

(12) United States Patent
Mourlas et al.

(10) Patent No.: US 6,979,290 B2
(45) Date of Patent: Dec. 27, 2005

(54) APPARATUS AND METHODS FOR CORONARY SINUS ACCESS

(75) Inventors: Nicholas J. Mourlas, Mountain View, CA (US); Christian Scott Eversull, Palo Alto, CA (US); Stephen Arie Leeflang, Stanford, CA (US); Asha Shrinivas Nayak, Menlo Park, CA (US); David John Miller, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 181 days.

(21) Appl. No.: 10/447,526

(22) Filed: May 29, 2003

(65) Prior Publication Data

US 2004/0097788 A1      May 20, 2004

Related U.S. Application Data

(60) Provisional application No. 60/384,262, filed on May 30, 2002.

(51) Int. Cl.[7] .............................................. A61B 1/04
(52) U.S. Cl. ........................ 600/115; 600/116; 600/104
(58) Field of Search ....................... 600/104, 114–116, 600/153, 156, 160

(56) References Cited

U.S. PATENT DOCUMENTS

| | | |
|---|---|---|
| 1,060,665 A | 5/1913 | Bell |
| 2,574,840 A | 11/1951 | Pieri et al. |
| 2,688,329 A | 9/1954 | Wallace |
| 3,162,190 A | 12/1964 | Gizzo |
| 3,974,834 A | 8/1976 | Kane |
| 4,033,331 A | 7/1977 | Guss et al. |
| 4,224,929 A | 9/1980 | Furihata |
| 4,470,407 A | 9/1984 | Hussein |
| 4,619,247 A | 10/1986 | Inoue et al. |
| 4,689,041 A | 8/1987 | Corday et al. |
| 4,717,387 A | 1/1988 | Inoue et al. |
| 4,723,936 A | 2/1988 | Buchbinder et al. |
| 4,779,611 A | 10/1988 | Grooters et al. |
| 4,781,681 A | 11/1988 | Sharrow et al. |

(Continued)

FOREIGN PATENT DOCUMENTS

EP       0283661 A3      9/1988

(Continued)

OTHER PUBLICATIONS

Osama Fujimura et al., Direct in Vivo Visualization . . . , Angiology, Mar. 1995, pp. 201-209.

(Continued)

*Primary Examiner*—Beverly M. Flanagan
(74) *Attorney, Agent, or Firm*—Cohen Sakaguchi & English LLP; William A. English

(57) ABSTRACT

An apparatus for locating morphological features within a body cavity includes a catheter including proximal and distal ends, a transparent balloon carried on the distal end, and an optical imaging assembly carried on the distal end for imaging through the balloon. The balloon includes a channel extending therethrough to a lumen extending through the catheter. A guidewire or other localization member is received in the lumen that is extendabe through the channel. During use, the catheter is inserted into a right atrium of a heart, and the balloon is expanded and placed against the wall of the heart to locate the coronary sinus. Sufficient force is applied to clear blood between the surface and the wall and clear the field of view of the imaging assembly. The catheter is manipulated to locate the coronary sinus, whereupon the localization member is advanced into the coronary sinus.

57 Claims, 18 Drawing Sheets

U.S. PATENT DOCUMENTS

| | | | |
|---|---|---|---|
| 4,784,113 A | 11/1988 | Mackin |
| 4,960,411 A | 10/1990 | Buchbinder |
| 4,961,738 A | 10/1990 | Mackin |
| 4,976,710 A | 12/1990 | Mackin |
| 5,029,574 A | 7/1991 | Shimamura et al. |
| 5,090,959 A | 2/1992 | Samson et al. |
| 5,116,317 A | 5/1992 | Carson, Jr. et al. |
| 5,188,596 A | 2/1993 | Condon et al. |
| 5,203,772 A | 4/1993 | Hammerslag et al. |
| 5,246,420 A | 9/1993 | Kraus et al. |
| 5,254,088 A | 10/1993 | Lundquist et al. |
| 5,271,383 A | 12/1993 | Wilk |
| 5,273,535 A | 12/1993 | Edwards et al. |
| 5,318,525 A | 6/1994 | West et al. |
| 5,346,504 A | 9/1994 | Ortiz et al. |
| 5,358,478 A | 10/1994 | Thompson et al. |
| 5,389,073 A | 2/1995 | Imran |
| 5,391,147 A | 2/1995 | Imran et al. |
| 5,409,469 A | 4/1995 | Schaerf |
| 5,409,483 A | 4/1995 | Campbell et al. |
| 5,447,497 A | 9/1995 | Sogard et al. |
| 5,489,270 A | 2/1996 | van Erp |
| 5,498,239 A | 3/1996 | Galel et al. |
| 5,593,405 A | 1/1997 | Osypka |
| 5,713,867 A | 2/1998 | Morris |
| 5,738,649 A | 4/1998 | Macoviak |
| 5,752,518 A | 5/1998 | McGee et al. |
| 5,762,604 A | 6/1998 | Kieturakis |
| 5,857,760 A | 1/1999 | Pelton |
| 5,876,373 A | 3/1999 | Giba et al. |
| 5,876,426 A | 3/1999 | Kume et al. |
| 6,035,224 A | 3/2000 | West |
| 6,086,557 A | 7/2000 | Morejohn et al. |
| 6,099,498 A | 8/2000 | Addis |
| 6,110,145 A | 8/2000 | Macoviak |
| 6,122,552 A | 9/2000 | Tockman |
| 6,178,346 B1 | 1/2001 | Amundson et al. |
| 6,562,049 B1 | 5/2003 | Norlander et al. |
| 6,585,718 B2 | 7/2003 | Hayzelden et al. |
| 6,592,581 B2 | 7/2003 | Bowe |
| 6,610,007 B2 | 8/2003 | Betson et al. |
| 6,616,628 B2 | 9/2003 | Hayzelden |
| 6,730,058 B2 | 5/2004 | Hayzelden |
| 6,743,227 B2 | 6/2004 | Seraj et al. |
| 6,755,812 B2 | 6/2004 | Peterson et al. |
| 6,783,510 B1 | 8/2004 | Gibson et al. |
| 6,800,056 B2 | 10/2004 | Tartaglia et al. |
| 2003/0092995 A1 | 5/2003 | Thompson |

FOREIGN PATENT DOCUMENTS

| | | |
|---|---|---|
| WO | WO 97/40880 | 11/1997 |
| WO | WO 00/24310 | 5/2000 |
| WO | WO 01/49356 | 7/2001 |
| WO | WO 01/72368 A2 | 10/2001 |
| WO | WO 03/039350 A2 | 5/2003 |
| WO | WO 03/053491 A2 | 7/2003 |
| WO | WO 03/073942 A2 | 9/2003 |

OTHER PUBLICATIONS

Osama Fujimura et al., Direct in Vivo Visualization . . . , European Heart Journal, Apr. 1994, p. 534-40.

Chien-Suu Kuo et al., In Vivo Angioscopic Visualization . . . , American Heart Journal, Jan. 1994, p. 187.

Km Moser et al., Angioscopic visualization of pulmnary emboli, Chest, Feb. 1980, pp. 198-201.

Moser, Shure, Harrell & Tulumello; Angioscopic Visualization of Pulmonary Emboli; Chest, 77:2, Feb. 1980,.

Kuo & Koch; In vivo angioscopic visualization of right heart structure in dogs . . . ; American Heart Journal, Jan. 1994; 127:187-97; Mosby-Year book, Inc.

Fujimura, Lawton & Koch; Direct in vivo visualization of right cardiac anatomy by fibreoptic endoscopy . . . ; European Heart Journal (1994) 15:534-40; European Society of Cardio.

Fujimura, Lawton & Koch; Direct in vivo visualization . . . Hemodynamic Effects . . . ; The Journal of Vascular Diseases; Mar. 1995; vol. 46, No. 3, pp. 201-209; Westminster Publi.

Vadimovich & Samuilovna; A Method of Endoscopic Investigation of Vascular Structures . . . ; The Heart Surgery Forum #1999-93916 2(2):136-38, 1999 Forum Multimedia Publishing, LLC.

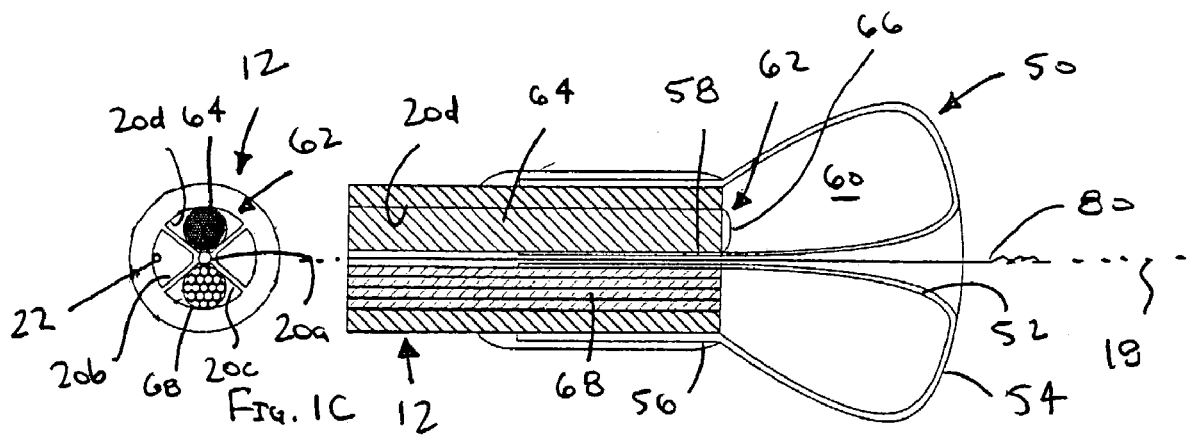
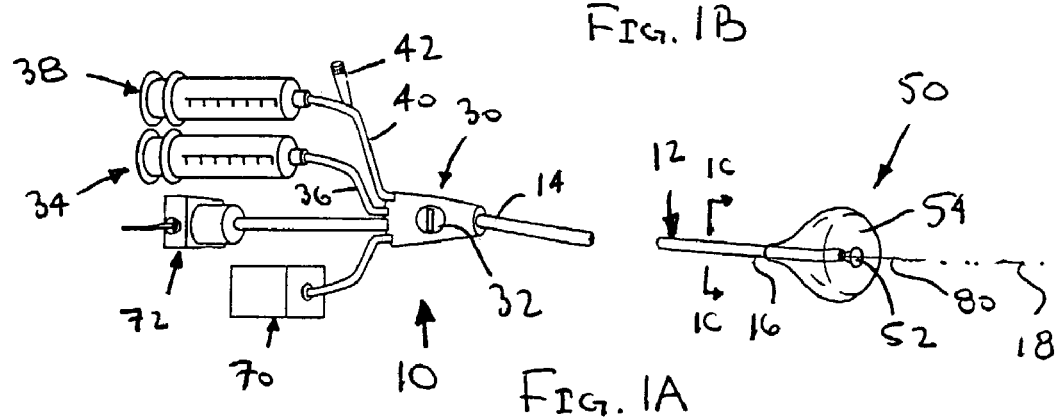
FIG. 1C  FIG. 1B  FIG. 1A
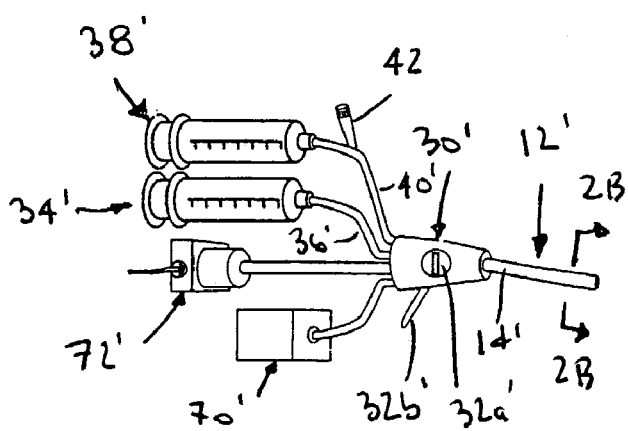
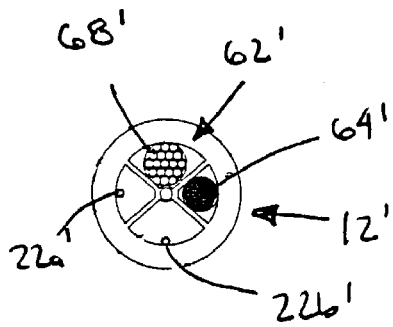
FIG. 2A  FIG. 2B

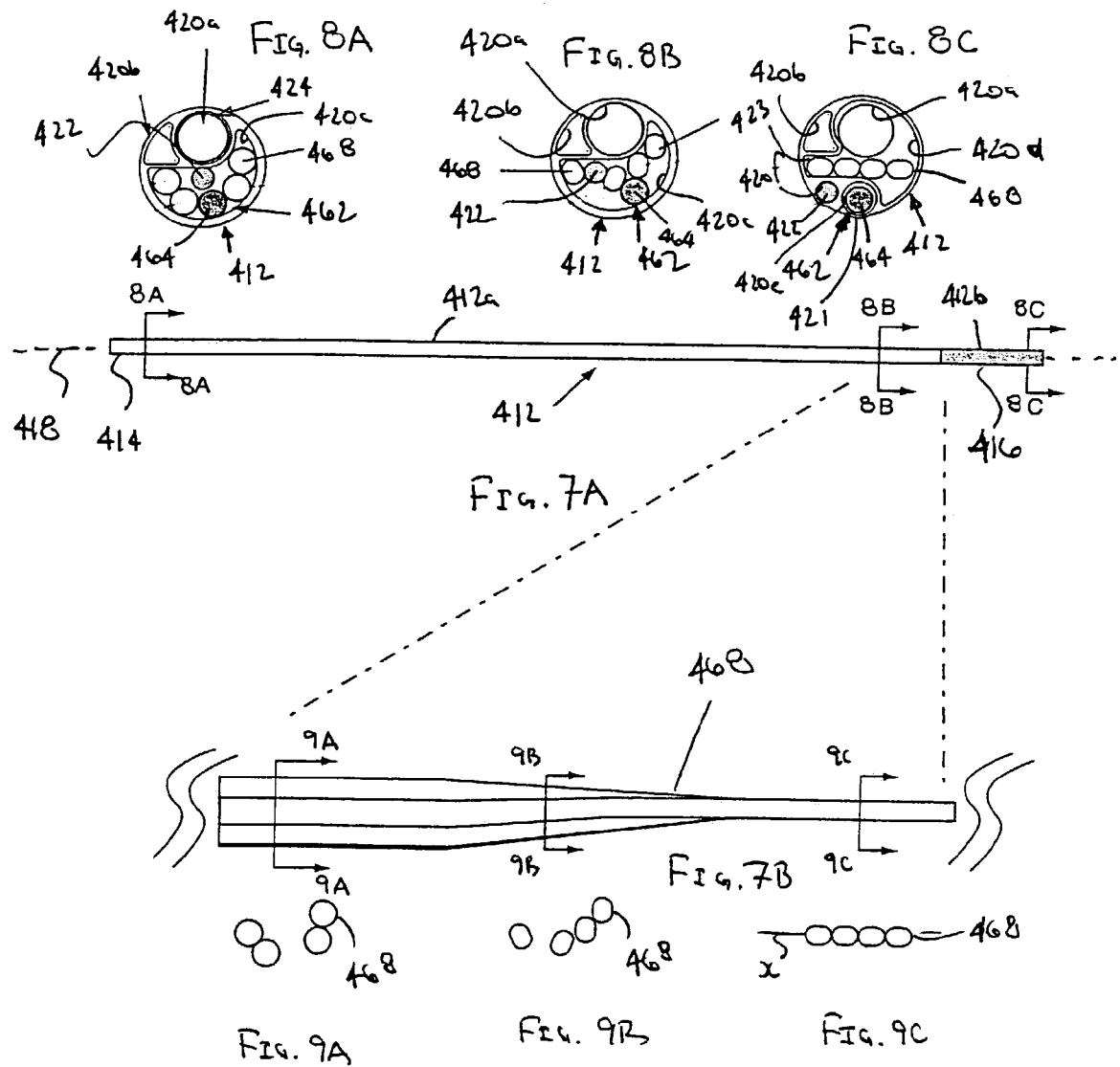

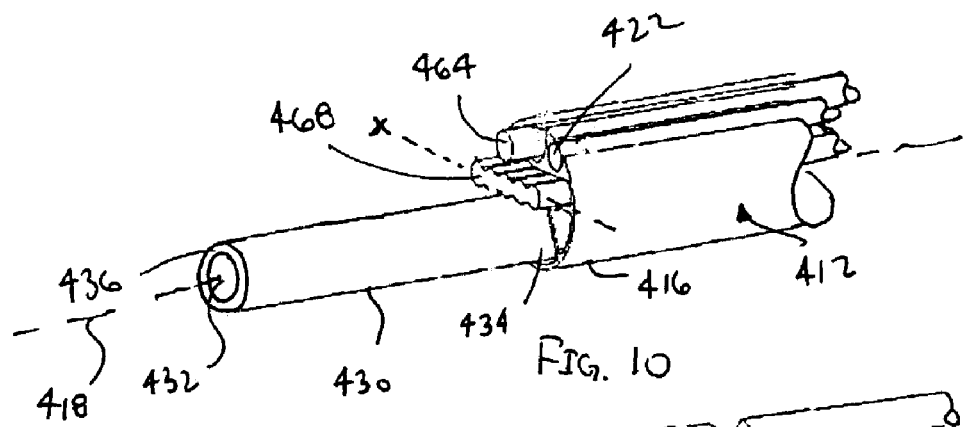
FIG. 10
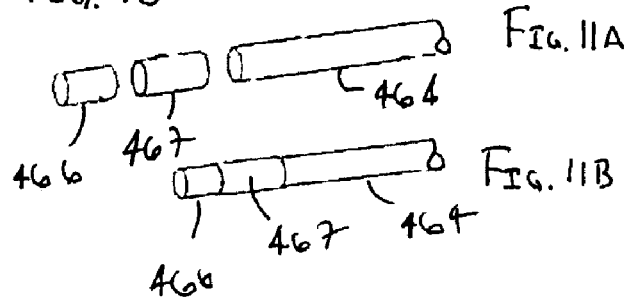
FIG. 11A
FIG. 11B
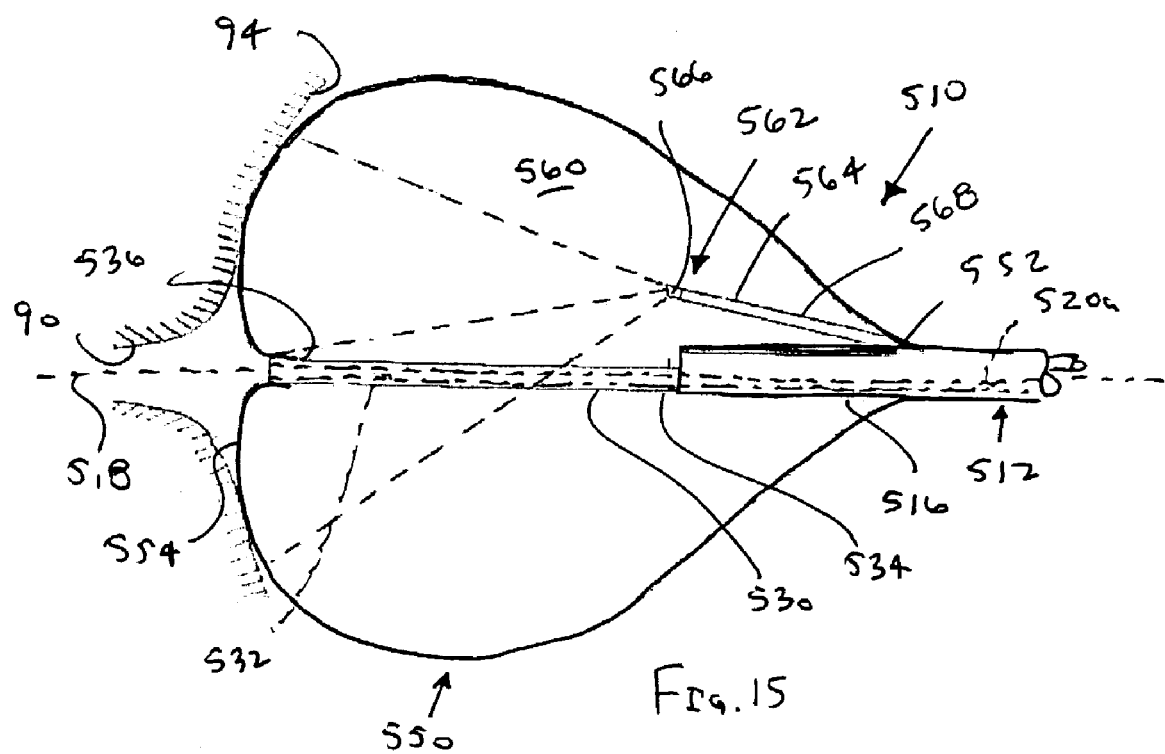
FIG. 15

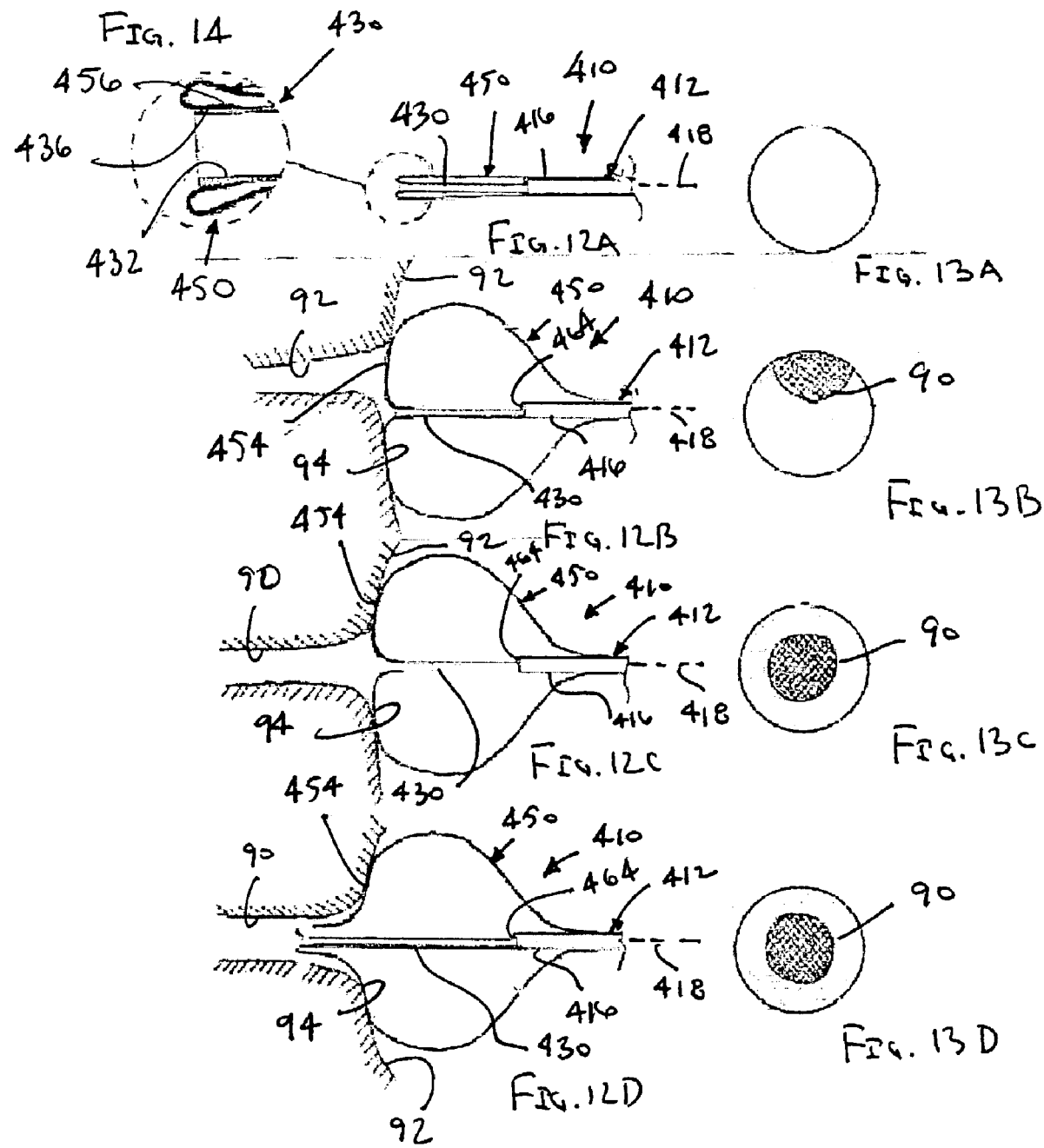

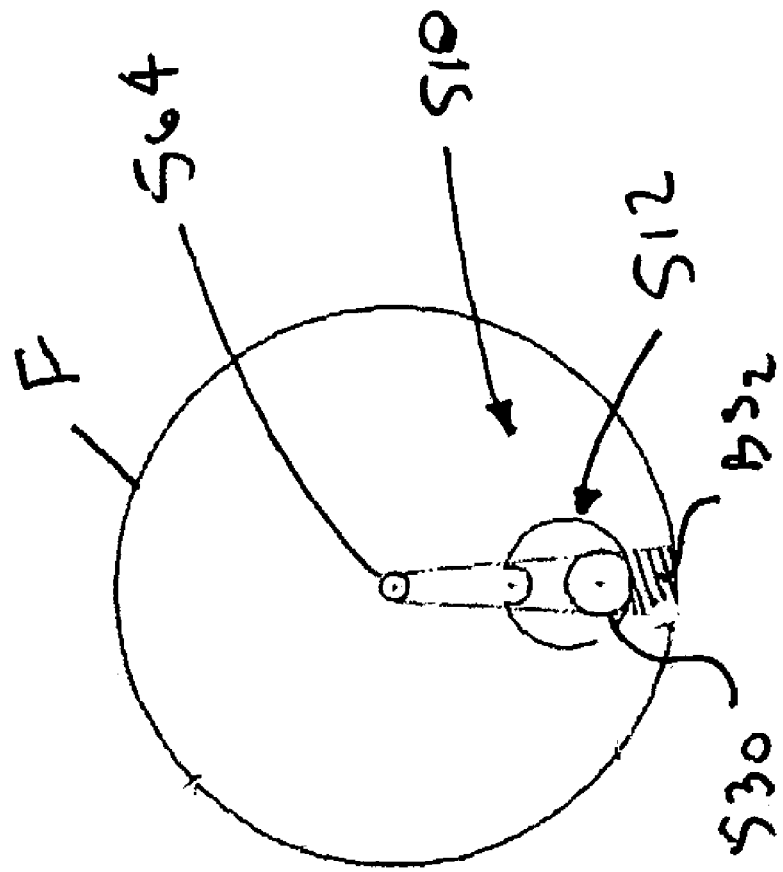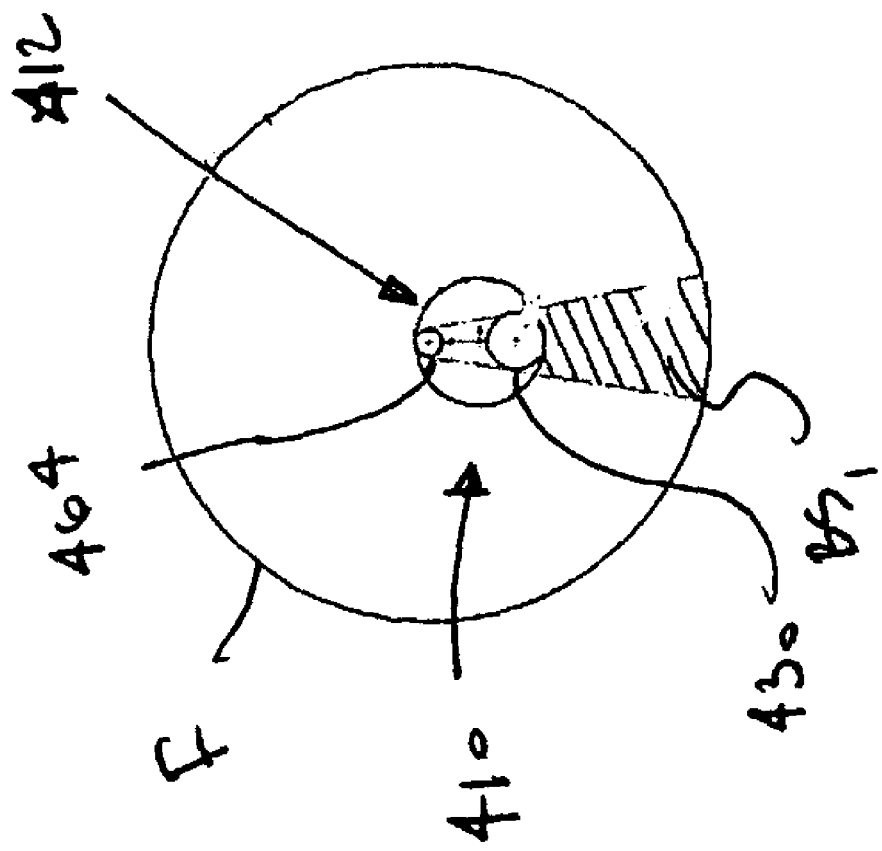

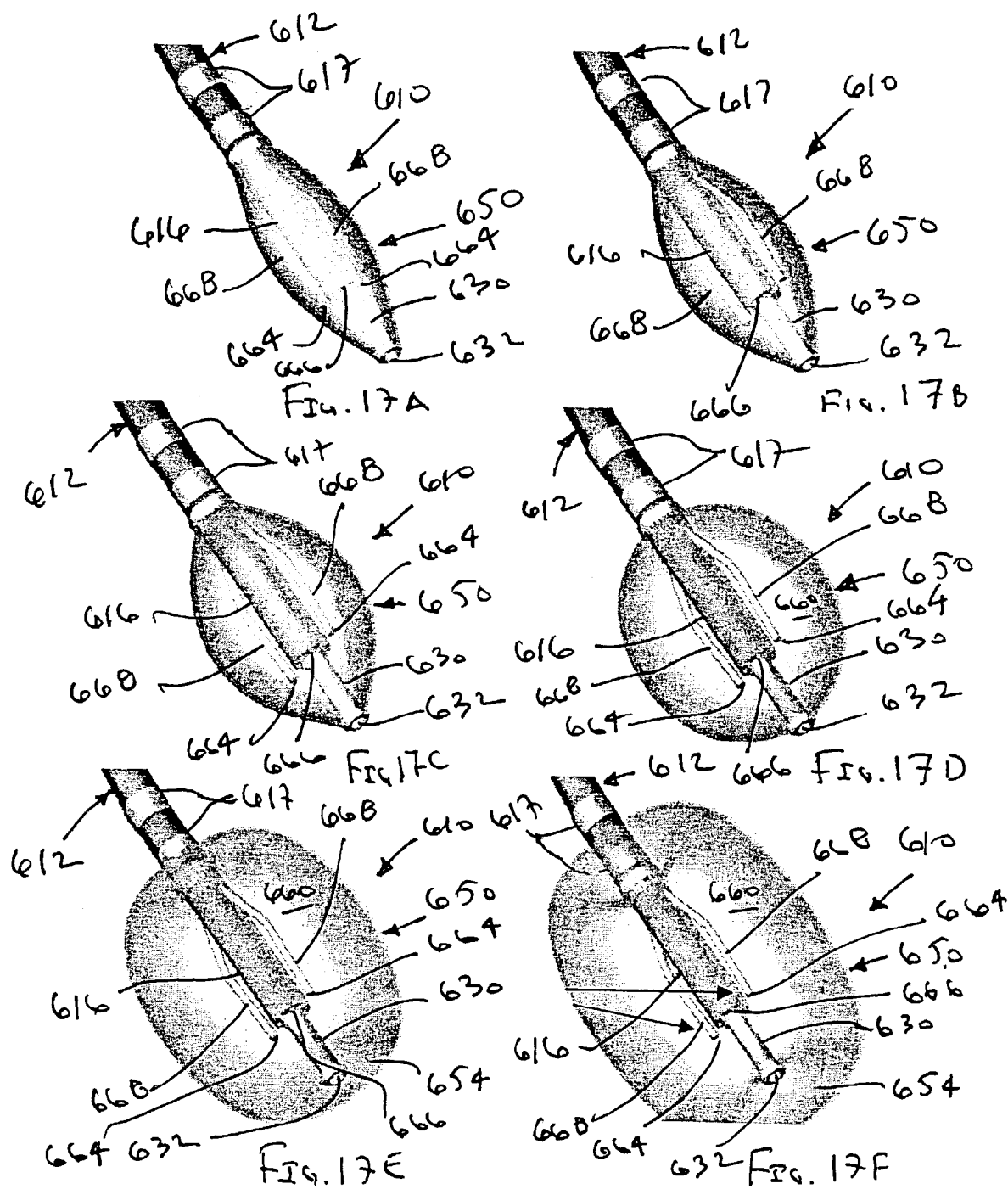

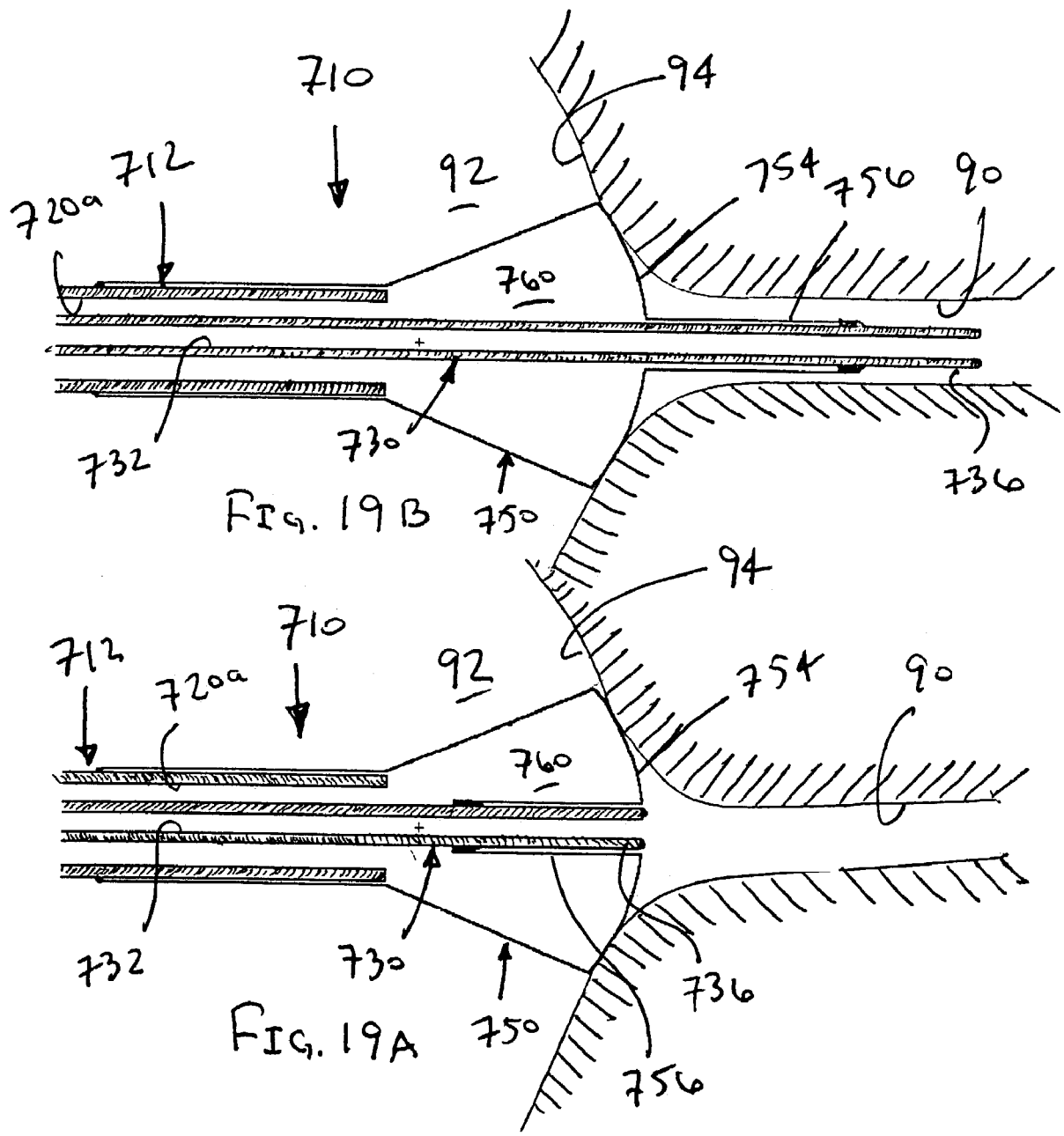

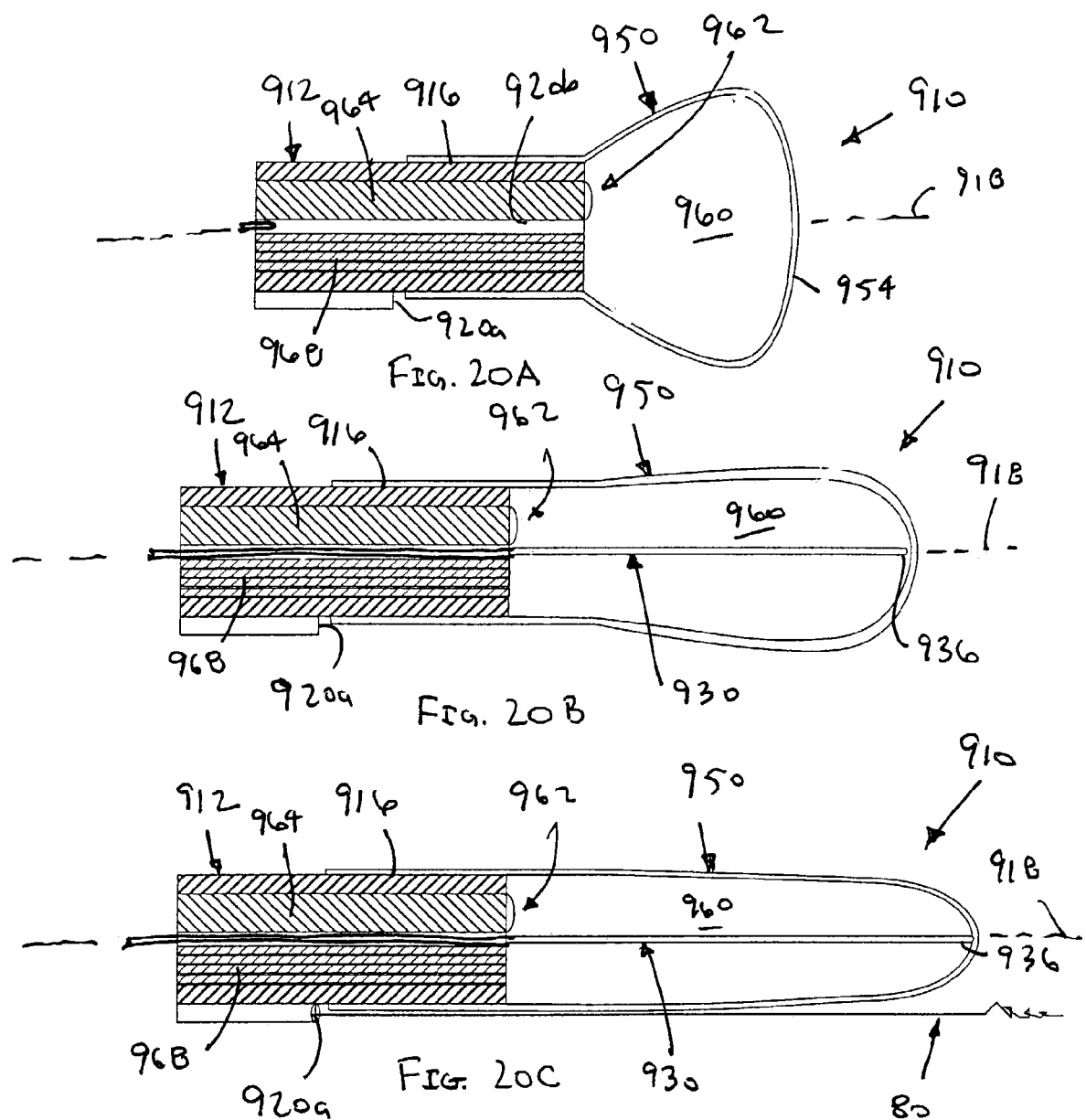

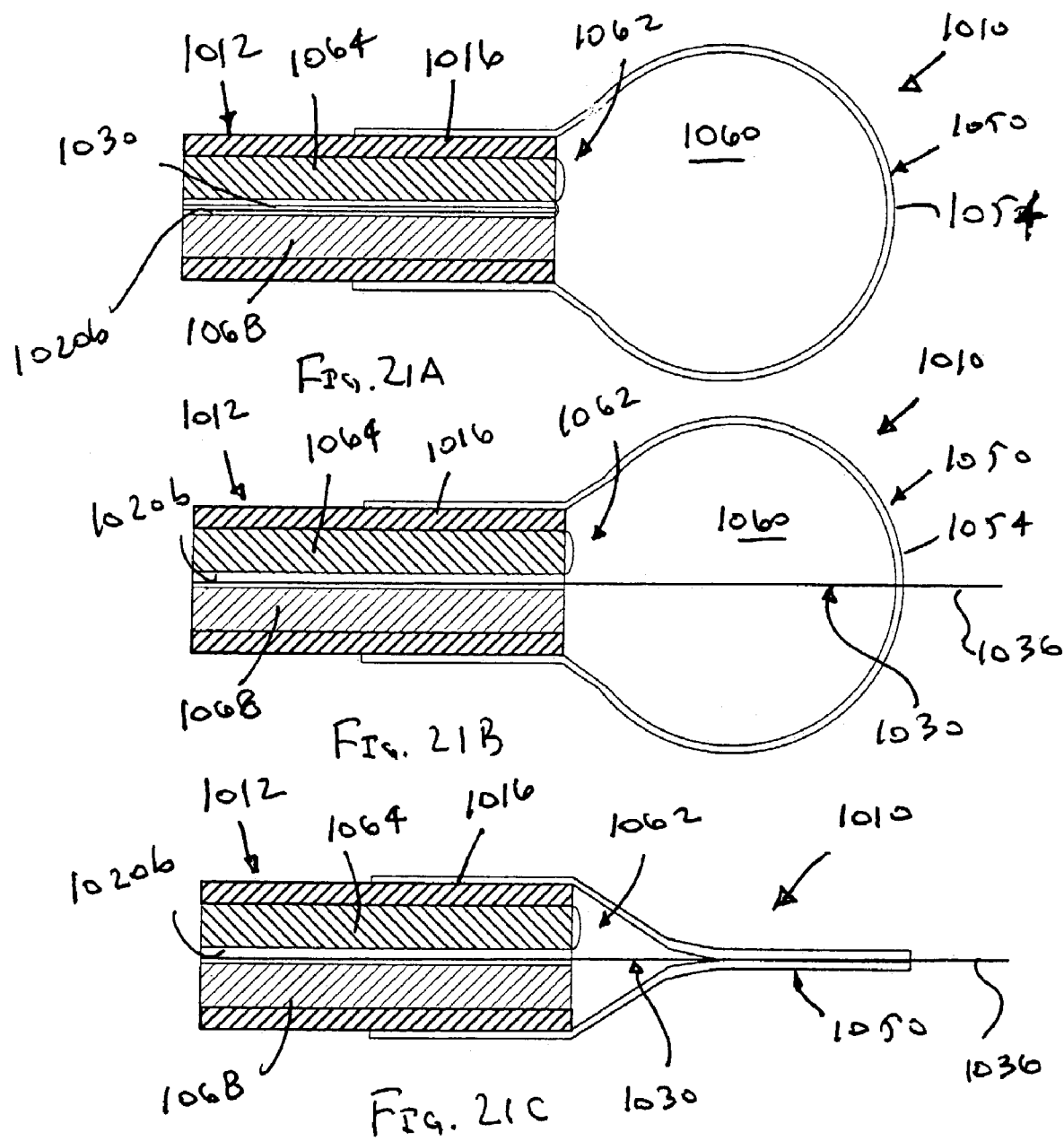

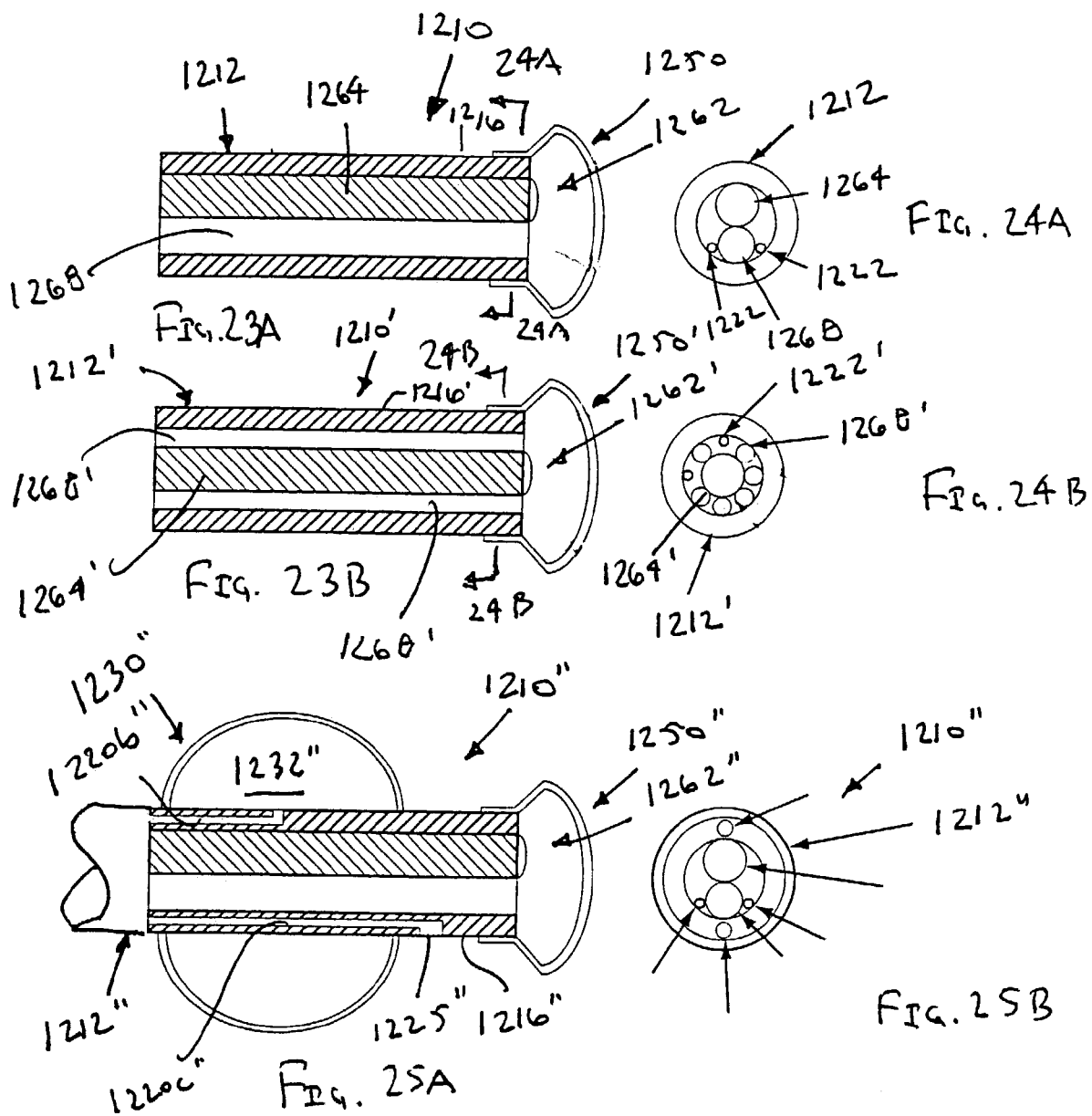

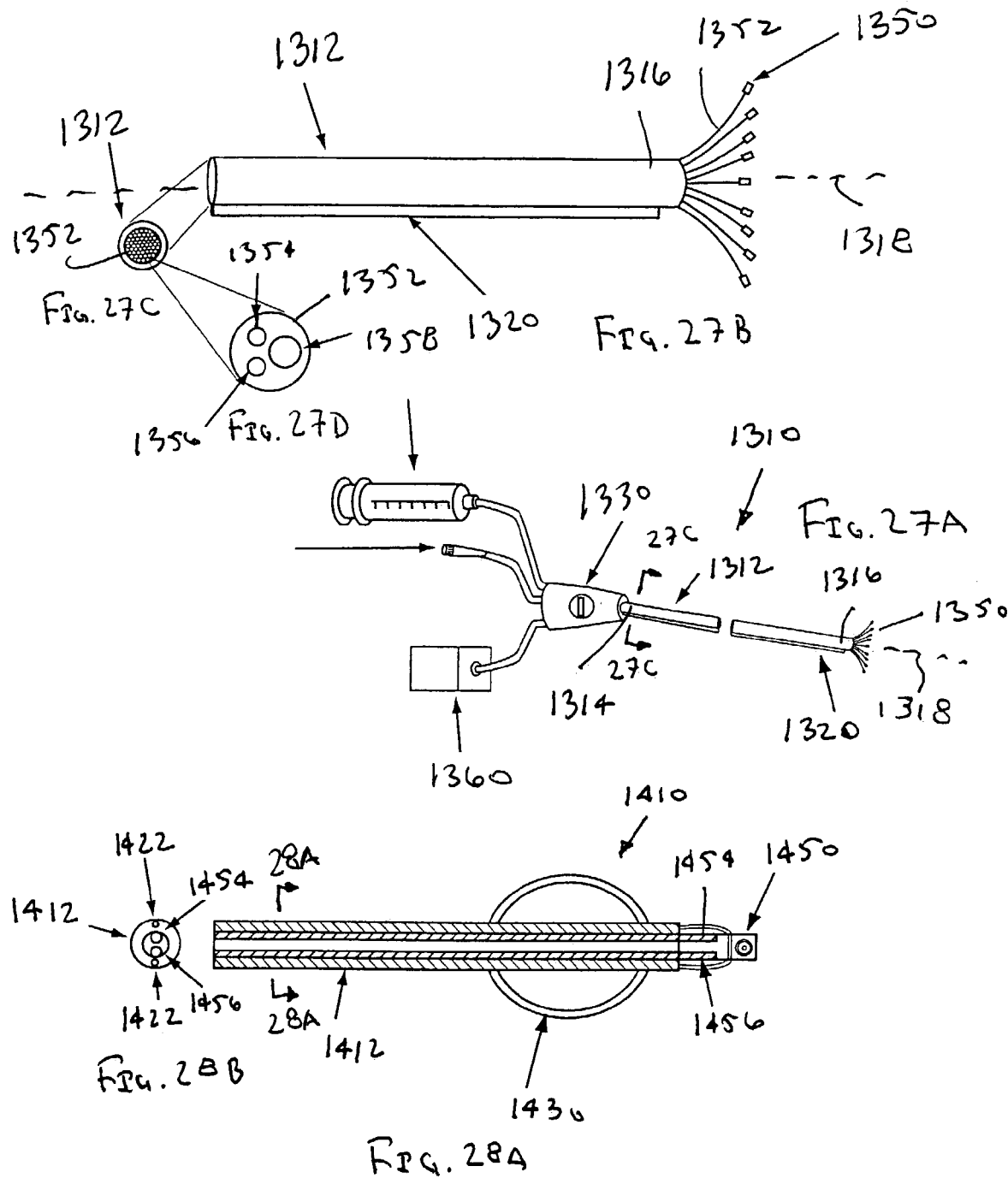

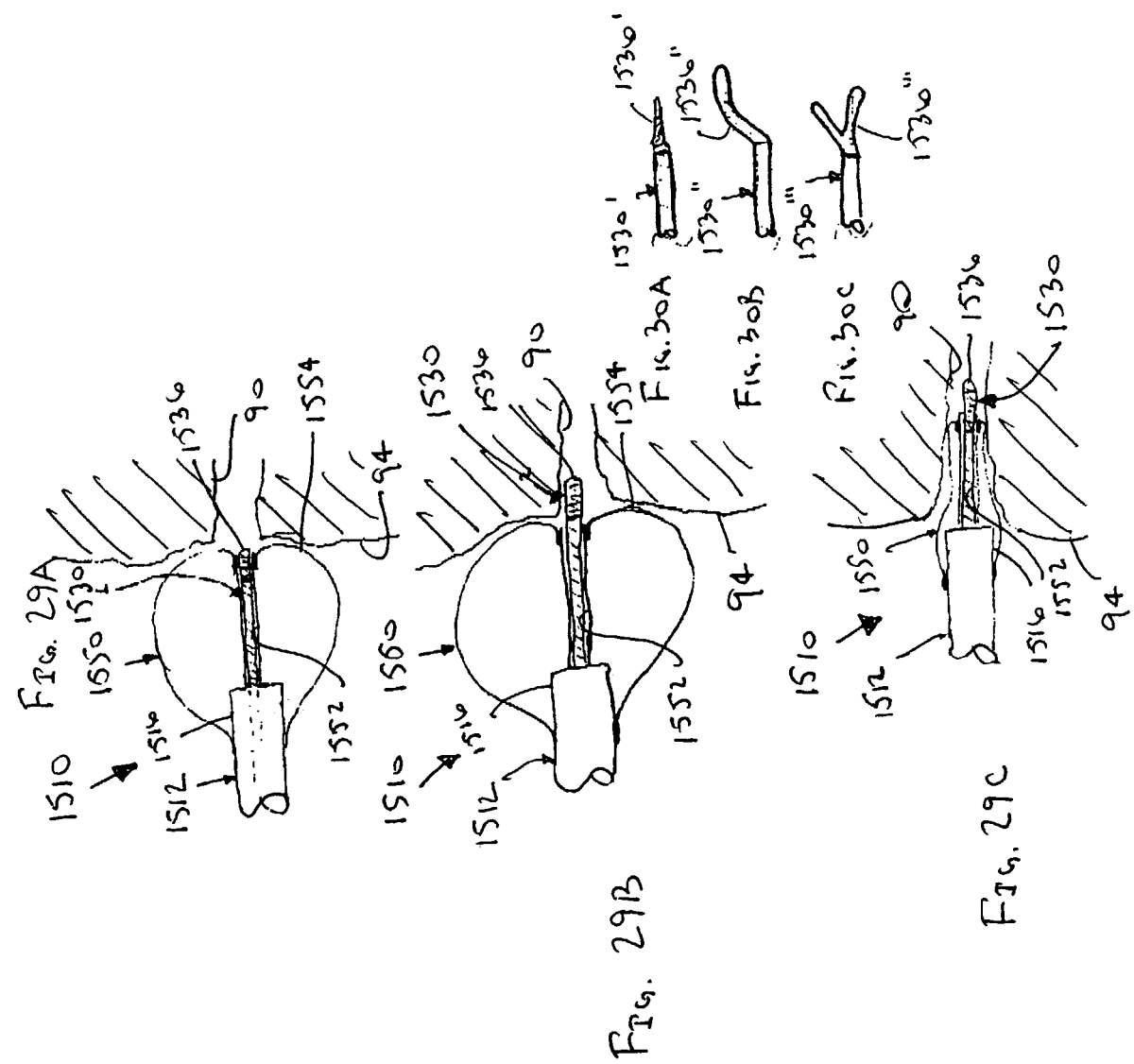

APPARATUS AND METHODS FOR CORONARY SINUS ACCESS

This application claims benefit of provisional application Ser. No. 60/384,262, filed May 30, 2002, the disclosure of which is expressly incorporated by reference herein.

FIELD OF THE INVENTION

The present invention relates generally to apparatus and methods for visualizing and/or cannulating body lumens, and, more particularly, to visualizing and cannulating a coronary sinus ostium of a heart, e.g., for delivering one or more instruments and/or fluids into coronary veins.

BACKGROUND

Minimally invasive procedures have been implemented in a variety of medical settings, e.g., for vascular interventions, such as angioplasty, stenting, embolic protection, electrical heart stimulation, heart mapping and visualization, and the like. One such procedure involves delivering an electrical lead into a coronary vein of a patient's heart that may be used to electrically stimulate the heart.

During such procedures, instruments, fluids, and/or medicaments may be delivered within a patient's vasculature using visualization tools, such as x-ray, fluoroscopy, ultrasound imaging, endoscopy, and the like. In many procedures, it may be desired to deliver instruments through opaque fluids, such as blood, or other materials. Endoscopes have been suggested that include devices for displacing these materials from an optical path, e.g., by introducing a clear fluid from the endoscope in an attempt to clear its field of view. Yet there are still improvements that may be made to such devices.

Accordingly, apparatus and methods for imaging within body lumens and/or for delivering instruments and/or fluids into a patient's body would be useful.

SUMMARY OF THE INVENTION

The present invention is directed to apparatus and methods for delivering instruments and/or fluids within a patient's body, and, more particularly, to apparatus and methods for visualizing, accessing, and/or cannulating body lumens, such as a coronary sinus ostium of a heart, e.g., for delivering electrical leads, devices, wire, or other instruments, medicaments, fluids, and/or other agents, e.g., into a coronary vein.

In accordance with one aspect of the present invention, an apparatus is provided for locating morphological features within a body cavity that may include a flexible tubular member including a proximal end, a distal end having a size for introduction into a body cavity, and defining a longitudinal axis extending between the proximal and distal ends. An optical imaging assembly may be carried by the distal end of the tubular member for imaging beyond the distal end.

A substantially transparent displacement member may also be carried by the distal end of the tubular member that at least partially surrounds the optical imaging assembly. In one embodiment, the displacement member may be an expandable member, e.g., a compliant or noncompliant balloon that extends from the distal end of the tubular member. Optionally, the expandable member may include a channel extending through an interior of the expandable member and/or communicating with a cannulation lumen extending through the tubular member.

In addition, the apparatus may include a localization member slidably received in a cannulation lumen of the tubular member. The localization member may be movable beyond the distal end of the tubular member for temporarily localizing the distal end of the tubular member at a morphologic feature within a body cavity. For example, where the expandable member includes a channel communicating with the cannulation lumen, the localization member may be movable from a retracted position proximal to the surface through the channel to a deployed position beyond the surface for localizing the distal end of the tubular member. Optionally, the localization member may terminate in a distal tip configured for engaging a morphological feature, e.g., a tapered distal tip, a forked distal tip, and a steerable distal tip.

Optionally, the apparatus may also include a capture device coupled to the proximal end of the tubular member and/or coupled to the optical imaging assembly for acquiring images obtained using the optical imaging assembly. For example, the capture device may include a display, a processor for processing the acquired images, and/or memory for storing the acquired images.

In accordance with another aspect of the present invention, an apparatus is provided for accessing a coronary sinus ostium extending from a right atrium of a heart. The apparatus may include a flexible tubular member including a proximal end, a distal end having a size for introduction into a right atrium, and a cannulation lumen extending between the proximal and distal ends, thereby defining a longitudinal axis. A localization member may be slidably received in the cannulation lumen, the localization member being movable beyond the distal end of the tubular member for temporarily localizing the distal end of the tubular member at a morphologic feature within a body cavity.

In addition, an array of oxygen sensors may be carried on the distal end of the tubular member for localizing a position of a coronary sinus ostium. In one embodiment, the oxygen sensors may be carried on ends of a plurality of filaments extending from the distal end of the tubular member. Alternatively, the oxygen sensors may be carried on an expandable member, e.g., a balloon, on the distal end of the tubular member.

In accordance with yet another aspect of the present invention, an apparatus for imaging within a body lumen that may include a flexible tubular member including proximal and distal ends defining a longitudinal axis therebetween, an expandable member on the distal end of the tubular member, and an optical imaging element disposed within the interior of the expandable member, the imaging element extending from the distal end of the tubular member in a direction at least partially transversely relative to the longitudinal axis.

In one embodiment, a channel may extend through the expandable member that communicates with a lumen extending between the proximal and distal ends of the tubular member. A source of fluid may be coupled to the proximal end of the tubular member, the source of fluid communicating with the lumen for delivering fluid through the channel to a location beyond the expandable member. In addition, or alternatively, an elongate member may be insertable through the lumen such that a distal end of the elongate member may be extended through the channel to a location beyond the expandable member.

Preferably, the lumen and channel extend substantially concentrically along a central longitudinal axis of the tubular member. Alternatively, the lumen may extend along a periphery of the tubular member, and the channel may extend along a wall of the expandable member.

In accordance with still another aspect of the present invention, an apparatus is provided for accessing a body lumen communicating with a body cavity that may include a flexible tubular member including a proximal end, a distal end having a size for introduction into a body cavity, and defining a longitudinal axis extending between the proximal and distal ends. An inner member may be slidably coupled to the tubular member, and a substantially transparent expandable member may be attached to the distal end of the tubular member and to a distal end of the inner member.

Te expandable member may be expandable from a contracted condition to an enlarged condition when fluid is introduced through the tubular member into an interior of the expandable member. The inner member may be slidable from a retracted position wherein a distal end of the expandable member at least partially everts into an interior of the expandable member, and an extended position wherein the expandable member defines a stabilizing element or nipple insertable into a body lumen extending from a body cavity for stabilizing the tubular member relative to the body lumen. Preferably, the apparatus also includes an optical imaging element carried by the distal end of the tubular member for imaging through the expandable member.

In accordance with yet another aspect of the present invention, a method is provided for cannulating a body lumen communicating with a body cavity of a patient. A distal end of a tubular member may be inserted into the body cavity, the tubular member including a substantially transparent expandable member thereon in a contracted condition. The expandable member may be expanded within the body cavity, and a surface of the expandable member may be placed in contact with a wall of the body cavity in order to image the wall through the expandable member. Preferably, sufficient force is applied to clear fluid, e.g., blood, from between the surface and the wall that may otherwise obscure imaging the wall.

The tubular member may be manipulated to move the expandable member along the wall, while imaging the wall through the expandable member, until the body lumen is identified. For example, the distal end of the tubular member may be steerable from the proximal end of the tubular member. Once the body lumen is identified, an instrument may be advanced from the tubular member into the body lumen. Alternatively, a localization member may be advanced at least partially into the body lumen to localize and/or stabilize the distal end of the tubular member.

In a preferred embodiment, the body cavity is a right atrium of a patient's heart, and the body lumen is a coronary sinus ostium. In this embodiment, the tubular member may be advanced from a peripheral vein through a vena cava to insert the distal end into the right atrium. Once the coronary sinus is cannulated, a procedure may be performed within the coronary veins via the coronary sinus. For example, the coronary sinus may be occluded and contrast injected to obtain a venogram of the coronary veins. In addition or alternatively, a guidewire may be advanced through the tubular member into the coronary sinus, e.g., to provide a rail for other instruments. In one embodiment, an electrical lead, e.g., for a pacemaker, may be delivered into a coronary vein via the coronary sinus using the tubular member and/or instruments introduced into the coronary sinus via the tubular member and/or guidewire.

Other objects and features of the present invention will become apparent from consideration of the following description taken in conjunction with the accompanying drawings.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 1A is a perspective view of a first preferred embodiment of an apparatus for cannulating a body lumen, in accordance with the present invention.

FIG. 1B is a cross-sectional detail of a distal end of the apparatus of FIG. 1A, showing a guidewire inserted through the apparatus.

FIG. 1C is a cross-section of the apparatus of FIG. 1A, taken along line 1C—1C.

FIG. 2A is a perspective view of an alternative embodiment of the apparatus of FIG. 1A, having two degrees of steering.

FIG. 2B is a cross-section of the apparatus of FIG. 2A, taken along line 2B—2B.

FIG. 7A is a side view of a catheter that may be included in the apparatus of FIG. 6.

FIG. 7B is a side view detailing a set of light guides that may be included in the catheter of FIG. 7A.

FIGS. 8A–8C are cross-sections of the catheter of FIG. 7, taken along lines 8A—8A, 8B—8B, and 8C—8C, respectively.

FIGS. 9A–9C are cross-sections of the light guides of FIG. 7B, taken along lines 9A—9A, 9B—9B, and 9C—9C, respectively.

FIG. 10 is a perspective detail of the apparatus of FIGS. 6 and 7A, with the balloon omitted for clarity.

FIGS. 11A and 11B are exploded and perspective views of a optical fiber bundle having a lens attached thereto.

FIGS. 12A–12D are partial cross-sectional views, showing a method for cannulating a body lumen communicating with a body cavity using the apparatus of FIGS. 6–10.

FIGS. 13A–13D show representative images that may be seen during respective steps of the cannulation method shown in FIGS. 12A–12D.

FIG. 14 is a cross-section detail showing a balloon attached to a tubular member.

FIG. 15 is a partial cross-sectional side view of a distal end of yet another embodiment of an apparatus including an off-axis imaging element, in accordance with the present invention.

FIGS. 16A and 16B are end views of the apparatus of FIGS. 6 and 15, respectively, showing an improved field of view obtaining using an off-axis imaging element.

FIGS. 17A–17F are perspective views of an alternative embodiment of an apparatus including a plurality of off-axis imaging elements.

FIGS. 19A and 19B are cross-sectional side views, showing a method for cannulating a body lumen, in accordance with the present invention.

FIGS. 20A–20C are cross-sectional side views of yet another embodiment of an apparatus for cannulating a body lumen, in accordance with the present invention.

FIGS. 21A–21C are cross-sectional side views of still another embodiment of an apparatus for cannulating a body lumen, in accordance with the present invention.

FIGS. 23A and 23B are cross-sectional side views of alternative embodiments of an apparatus for cannulating a body lumen, in accordance with the present invention.

FIGS. 24A and 24B are end views of the apparatus of FIGS. 23A and 23B, respectively.

FIG. 25A is a cross-sectional side view of another embodiment of an apparatus for cannulating a body lumen, in accordance with the present invention.

FIG. 25B is an end view of the apparatus of FIG. 25A.

FIG. 27A is a perspective view of yet another embodiment of an apparatus for cannulating a body lumen, including a plurality of oxygen sensors, in accordance with the present invention.

FIG. 27B is a perspective detail, showing a catheter of the apparatus of FIG. 27A.

FIG. 27C is a cross-sectional view of the apparatus of FIGS. 27A and 27B, taken along line 27C—27C.

FIG. 27D is a detail of a tubular segment extending to an oxygen sensor of the apparatus of FIGS. 27A–27C.

FIG. 28A is a cross-sectional side view of still another embodiment of an apparatus for cannulating a body lumen, including an oxygen center and an occlusion balloon.

FIG. 28B is a cross-section of the apparatus of FIG. 28A, taken along line 28A—28A.

FIGS. 29A–29C are cross-sectional views, showing a method for cannulating a coronary sinus ostium extending from a right atrium of a heart, in accordance with the present invention.

FIGS. 30A–30C are details, showing alternate tips of a stabilization member that may be included in the apparatus shown in FIGS. 29A–29C.

DETAILED DESCRIPTION OF THE PREFERRED EMBODIMENTS

Figures 3A, 3B, 3C:
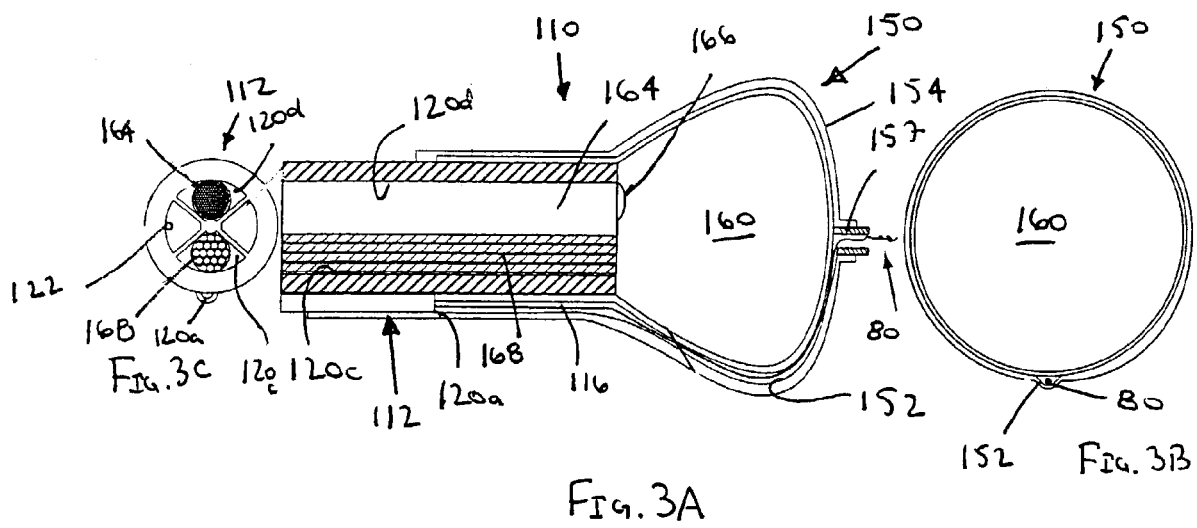
FIG. 3A is a cross-sectional detail, showing an alternative embodiment of an apparatus for cannulating a body lumen including a balloon, in accordance with the present invention.
FIGS. 3B and 3C are cross-sections of the apparatus of FIG. 3A, taken along lines 3B—3B, and 3C—3C, respectively.

Turning to the drawings, FIGS. 1A–1C show a first preferred embodiment of an apparatus 10 for imaging a body lumen, e.g., for visualizing, accessing, and/or cannulating a body lumen from a body cavity (not shown). In a preferred embodiment, as explained further below, the apparatus 10 may be used for imaging a wall of a right atrium of a heart, e.g., for visualizing, accessing, and/or cannulating a coronary sinus ostium, although the apparatus 10 may be used for visualizing, accessing, and/or cannulating other body lumens as well. Generally, as shown in FIG. 1A, the apparatus 10 may include a catheter or other elongate member 12, a balloon or other expandable member 50 on a distal end 16 of the catheter 12, and an imaging assembly 62 carried by the distal end 16 of the catheter 12 for imaging through the balloon 50.

The catheter 12 generally is an elongate tubular body including a proximal end 14, a distal end 16 having a size and shape for insertion into a patient's body, and a central longitudinal axis 18 extending between the proximal and distal ends 14, 16. The catheter 12 may include one or more lumens 20 also extending between the proximal and distal ends 14, 16, e.g., a cannulation lumen 20a, an inflation lumen 20b, and one or more lumens 20c, 20d (best seen in FIG. 1C) for the imaging assembly 62.

The catheter 12 may be substantially flexible, semi-rigid, and/or rigid along its length, and may be formed from a variety of materials, including plastic, metal and/or composite materials, as is well known to those skilled in the art. For example, the catheter 12 may be substantially flexible at the distal end 16 to facilitate advancement through tortuous anatomy, and/or may be semi-rigid or rigid at the proximal end 14 to enhance pushability of the catheter 12 without substantial risk of buckling or kinking.

Preferably, the catheter 12 is steerable, i.e., the distal end 16 may be controllably deflected transversely relative to the longitudinal axis 18. In the embodiment shown in FIGS. 1A–1C, a single pullwire or other steering element 22 may be provided, e.g., within one of the lumens 20, for steering the distal end 16 of the catheter 12 in one transverse plane (thereby providing one degree of freedom). Alternatively, in another embodiment, such as that shown in FIGS. 2A and 2B, two pullwires 22' may be provided for steering the distal end 16' of the catheter 12' in two orthogonal planes (thereby providing two degrees of freedom).

The pullwire(s) 22 may be a cable, wire, band, and the like that may be slidably disposed within a lumen, such as the inflation lumen 20b shown in FIG. 1C. The pullwire(s) 22 may be attached or otherwise fixed relative to the catheter 12 at a location adjacent the distal end 16, preferably offset radially outwardly from the central axis 18. Thus, when the pullwire 22 is pulled proximally, e.g., from the proximal end 14 of the catheter 12, a bending force may be applied to the distal end 16, causing the distal end 16 to bend transversely relative to the central axis 18.

The catheter 12 may also include a handle or other control mechanism 30 coupled to or otherwise provided on the proximal end 14 of the catheter 12. The handle 30 may include one or more steering controls 32 that may be actuated to steer the distal end 16 of the catheter 12. For example, as shown in FIG. 1, a dial 32 may be provided that may be coupled to the pullwire 22. The dial 32 may be rotated to apply a proximal force on the pullwire 22, thereby bending the distal end 16 of the catheter 12.

Alternatively, as shown in FIGS. 2A and 2B, a dial 32a' and a trigger 32b' may be provided on the handle 30' that may be coupled to respective pullwires 22a,' 22b.' Thus, the dial 32' may be rotated to bend the catheter 12' in a first direction and the trigger 32b' may be pulled to bend the catheter 12' in a second direction, preferably substantially perpendicular to the first direction. The steering control(s) may be biased, e.g., to return the distal end 32 or 32' of the catheter 12 or 12' to a generally straight configuration when the control(s) is(are) released. Alternatively, each steering control may be coupled to a pair of opposing pullwires opposite one another relative to the central axis (not shown) such that actuating the control in one direction bends the distal end one direction, while actuating the control in an opposite direction bends the distal end in an opposite direction. It will be appreciated that other control mechanisms and/or steering arrangements may be provided, including one, two, or more degrees of freedom, as are well known to those skilled in the art.

The handle 30 may also include ports and/or other connections for connecting other components to the catheter 12. It will be appreciated that any known connectors may be provided for permanently or temporarily connecting components to the catheter 12. For example, a luer lock connector may be used to connect tubing or other fluid-conveying components to the handle 30.

As shown in FIG. 1A, a syringe or other source of fluid 34, e.g., including saline, carbon dioxide, nitrogen, or air, may be connected via tubing 36 to the inflation lumen 20b (not shown, see FIG. 1C) for inflating the balloon 50. The syringe 34 may also provide a source of vacuum for deflating the balloon 50, as is known in the art. Another source of fluid 38, e.g., saline, and/or a therapeutic or diagnostic agent, may be connected via tubing 40 to the cannulation lumen 20a for delivering fluid beyond the distal end 16 of the catheter 12.

In addition, an access port 42 may also communicate with the cannulation lumen 20a, e.g., including a hemostatic seal and the like (not shown), for delivering one or more instruments (such as guidewire 80, shown in FIG. 1B) through the cannulation lumen 20a, as explained further below. Optionally, the handle 30 may include a shape, size, and/or contour (not shown) for facilitating manipulating the catheter 12 during use.

Returning to FIGS. 1A and 1B, a substantially transparent balloon 50 may be provided on the distal end 16 of the tubular member 12. The balloon 50 may be expandable from a contracted condition (not shown) to an enlarged condition when fluid is introduced into an interior 60 of the balloon 50. In the embodiment shown, a channel 52 may extend through the balloon 50 that communicates with a lumen 20 of the catheter 12, e.g., the cannulation lumen 20a. Preferably, the channel 52 extends through the balloon 50 concentrically with the central axis 18, as best seen in FIG. 1B.

In an exemplary embodiment, the balloon 50 may be formed from substantially noncompliant material, e.g., polytetrafluoroethylene (PTFE), expanded polytetrafluoroethylene (EPTFE), fluorinated ethylenepropylene (FEP), polyethylene teraphathalate (PET), urethane, olefins, and polyethylene (PE), such that the balloon 50 may expand to a predetermined shape when fully inflated to the enlarged configuration. Preferably, in the enlarged configuration, the balloon 50 may have a distal surface 54 that is substantially flat or otherwise configured for contacting a wall of a body cavity, such as the right atrium (not shown). Alternatively, as shown in FIGS. 19A and 19B, an apparatus 710 may be provided that carries a balloon 750 having a frustoconical shape and/or a convex distal surface 754.

The material may be sufficiently flexible and/or elastic such that the distal surface 54 may conform substantially to the wall of the body cavity. Preferably, the balloon 50 is also sufficiently noncompliant to displace blood or other fluid from between the distal surface 54 and the wall of the body cavity to facilitate imaging the wall through the balloon 50, as explained further below. Alternatively, the balloon 50 may be formed from compliant and/or elastomeric materials, such as silicone, latex, isoprene, and chronoprene.

In the exemplary embodiment shown in FIG. 1B, the balloon 50 may be formed from one or more panels that may be attached to one another, e.g., using an adhesive (such as an adhesive cured using ultraviolet ("UV") light), sonic welding, and/or heating, after lapping or butting adjacent panels together. Alternatively, the balloon 50 may be molded around or within a mold (not shown) having a desired shape for the balloon 50 in the enlarged condition.

The resulting balloon 50 may include a proximal end 56 that may be attached to an outer surface of the catheter 12, e.g., using an adhesive, heating, sonic welding, an interference fit, and/or an outer sleeve. The channel 52 may be formed from the same material as the rest of the balloon 50, and a proximal end 58 of the channel may be attached to the distal end 16 of the catheter 12, e.g., within or concentric with the cannulation lumen 20a. Alternatively, the channel may be formed from a semi-rigid or rigid tubular member, as shown in FIGS. 6–10, and described further below.

As best seen in FIG. 1B, the interior 60 of the balloon 50 may have a generally annular shape that preferably communicates with the inflation lumen 20b (not shown, see FIG. 1C) of the catheter 12. Substantially transparent inflation media, e.g., saline, carbon dioxide, nitrogen, air, and the like, may be introduced into the interior 60 of the balloon 50 to expand the balloon 50 towards the enlarged condition shown in FIGS. 1A and 1B. As used herein, "transparent" refers to any material and/or fluid that may permit sufficient light to pass therethrough in order to identify or otherwise visualize objects through the material and/or fluid. "Light" as used herein may refer to light radiation within the visible spectrum, but may also include other spectra, such as infrared ("IR") or ultraviolet ("UV") light.

Alternatively, the balloon and/or channel may have different configurations, such as that shown in FIGS. 3A–3C and 4. For example, as shown in FIGS. 3A–3C, an apparatus 110 is shown that includes a catheter 112 that may include one or more lumens, e.g., lumens 120c, 120d for receiving components of an imaging assembly 162 therethrough, similar to the previous embodiment. Unlike the previous embodiment, a cannulation lumen 120a extends along an outer surface of the catheter 112 that extends between a proximal end (not shown) to a distal end 116 of the catheter 112. The lumen 120a may be a separate tubular member attached to the catheter 112 or may be an integral part of the catheter 112, e.g., formed as a single extrusion.

A balloon 150 may be carried on the distal end 116 of the catheter 112 that defines an interior 160 communicating with an inflation lumen (not shown) that extends to the proximal end of the catheter 112, similar to the previous embodiment. A channel 152 may extend along a wall of the balloon 150 that communicates with the cannulation lumen 120a. The channel 152 may be defined by a panel of material attached to the balloon 150, similar to the materials and methods for making balloon 50, as described above. Alternatively, an inner balloon panel may be provided within an outer balloon panel and the panels may be attached to one another, e.g., along one or more seams defining the channel 152.

A nipple or annular collar 157 may be provided on the distal surface 154 of the balloon 150, e.g., to guide a guidewire 80 or other instrument out of the balloon 150, and/or to stabilize the device relative to a body lumen or other tissue structure (not shown). Thus, a guidewire 80 may be inserted into the cannulation lumen 120a from the proximal end of the catheter 112, the channel 152 guiding the guidewire 80 through the balloon 150 until it exits through the nipple 157 to a location beyond the distal surface 152 of the balloon 150.

Figure 4:
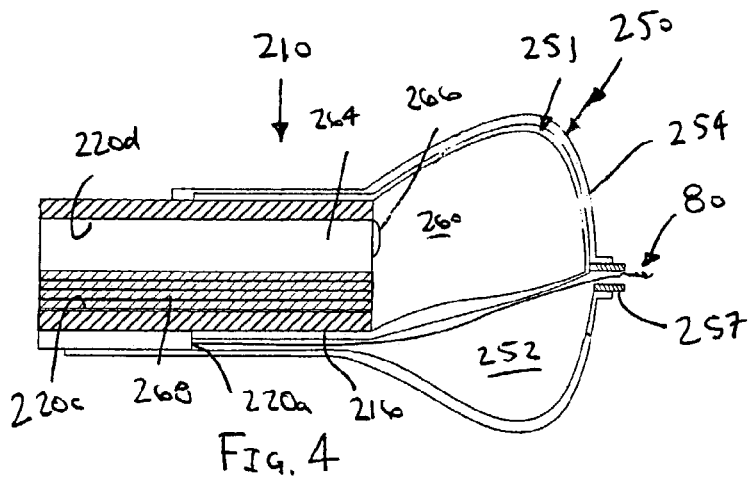
FIG. 4 is a cross-sectional detail, showing another alternative embodiment of an apparatus for cannulating a body lumen including a balloon, in accordance with the present invention.

In another alternative, shown in FIG. 4, an inner balloon 251 may be provided within an interior 260 of an outer balloon 250. The inner balloon 251 may be expandable to a size and/or shape that is smaller than the outer balloon 250, thereby defining a channel 252 between the balloons 251, 252. Thus, a guidewire 80 or other instrument (not shown) may be inserted into a cannulation lumen 220a, e.g., extending along an outer surface of the catheter 212. The guidewire 80 may enter the channel 252 between the balloons 251, 252 until it exits through a nipple 257, similar to the embodiment shown in FIGS. 3A–3C.

In a further alternative, a balloon may be provided without a channel extending therethrough, as shown, for example, in FIGS. 20A–22C, and described further below.

Figure 5A:
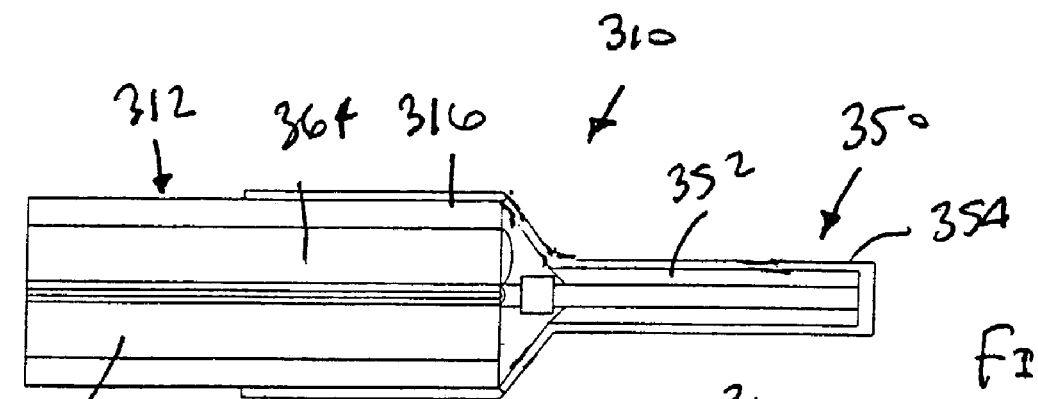
FIGS. 5A–5C are cross-sectional side views of an embodiment of a mechanically expandable member that may be substituted for an inflatable balloon in an apparatus, in accordance with the present invention.
Figure 5B:
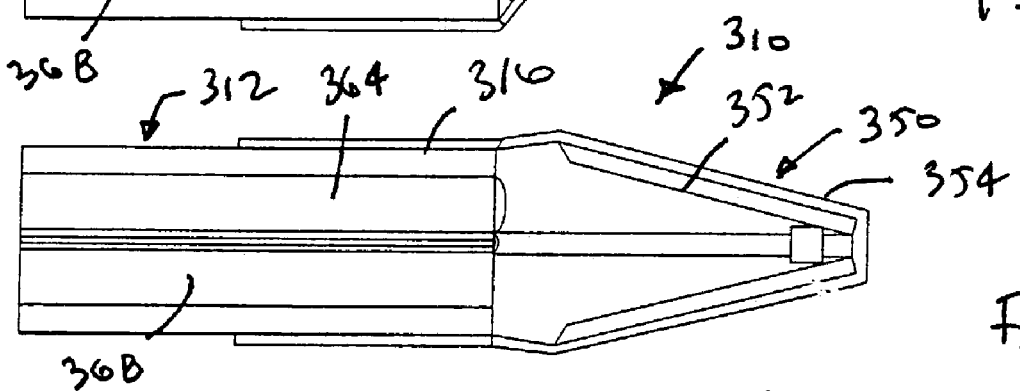
Figure 5C:
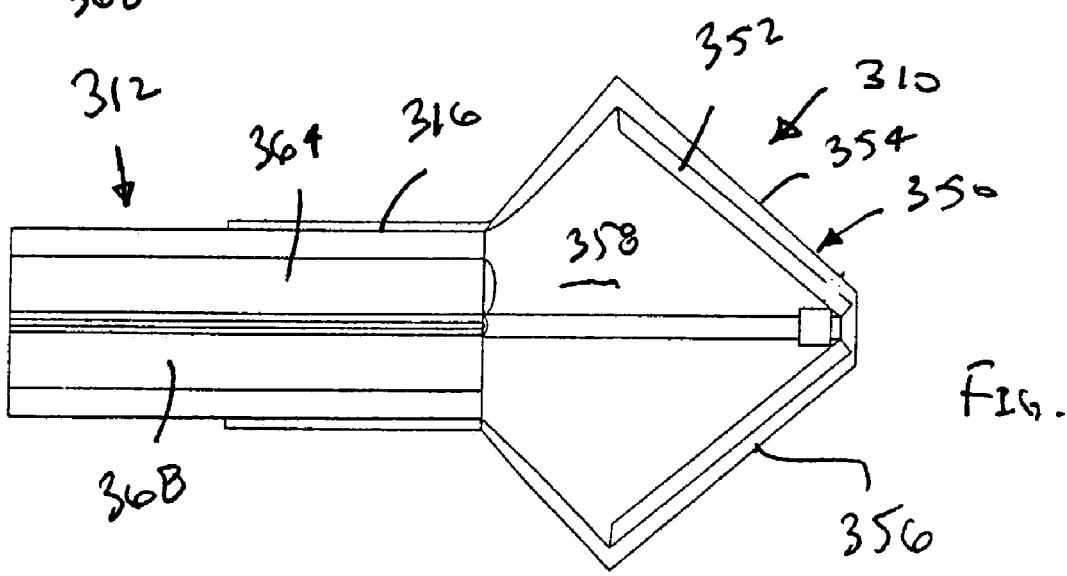

In yet another alternative, shown in FIGS. 5A–5C, an apparatus 310 may be provided that includes a mechanically expandable member 350 carried on a distal end 316 of a catheter 312. A frame 352 may be coupled to the distal end 316 that may support a substantially transparent, flexible membrane 354. The frame 352 may include a plurality of members that are movable away from and towards one another, thereby causing the membrane 354 to move between contracted and enlarged conditions.

The frame 352 may be actuated from a proximal end (not shown) of the catheter 312, e.g., to cause the frame 352 to expand radially outwardly, as shown in FIGS. 5B and 5C. As the frame 352 expands, the membrane 354 may provide a substantially transparent surface 356 through which an optical imaging assembly, e.g., including an optical fiber bundle 364 and/or a light guide 368, similar to that described further below, may obtain optical images. Optionally, an interior 358 of the membrane 354 may be filled with a substantially transparent fluid, similar to the balloons described above, to facilitate imaging through the expandable member 350.

Returning to FIGS. 1A–1C, the imaging assembly 62 generally includes an optical imaging element 64 that is exposed within the interior 60 of the balloon 50 for capturing light images through the balloon 50. In a preferred embodiment, the optical imaging element 64 includes a bundle of optical fibers, e.g. a coherent image bundle, that extends between the proximal and distal ends 14, 16 of the catheter 12, e.g., through the lumen 20d, as shown in FIG. 1C. Preferably, the fiber bundle 64 includes about ten thousand (10,000) optical fibers, although it may include between about one and fifty thousand (1,000–50,000) fibers in order to provide a desired resolution in the images obtained by the fiber bundle 64.

A lens 66, e.g., a GRIN or self-oc lens, may be coupled to the fiber bundle 64 in order to focus light from beyond the distal surface 54 of the balloon 50 onto the fiber bundle 64 in order to generate a resolved image at the proximal end of the fiber bundle 64, as is well known to those skilled in the art. Optionally, a directional prism or other optical element (not shown) may be provided for directing a field of view of the fiber bundle 64 as desired, as explained further below.

In addition, the imaging assembly 62 may include one or more light guides 68 carried by the distal end 16 of the catheter 12 for delivering light into the interior 60 and/or through the distal surface 54 of the balloon 50. Although a single light guide 68 is shown in FIGS. 1B and 1C, it will be appreciated that a plurality of light guides (not shown) may be provided in a common lumen or separate lumens (also not shown) within the catheter 12. The light guide(s) 68 may include a plurality of optical fibers, e.g., formed from acrylic and the like, that may extend to the proximal end 14 of the catheter 12. As shown in FIG. 1A, a source of light 70 may be coupled to the light guide(s) 68, e.g., via the handle 30, for delivering light through the light guide(s) 68 and into the balloon 50.

A device 72 may be coupled or otherwise provided at the proximal end 14 of the apparatus 10 for acquiring and/or capturing images obtained by the optical imaging assembly 62. For example, one or more lenses (not shown) may be coupled to the fiber bundle 64 for focusing and/or resolving light passing through the fiber bundle 64, e.g., to pass the image to the device 72. The device 72 may include a CCD, CMOS, and/or other device, known to those skilled in the art, e.g., to digitize or otherwise convent the light images from the fiber bundle 64 into electrical signals that may be transferred to a processor and/or display (not shown).

Figure 26:
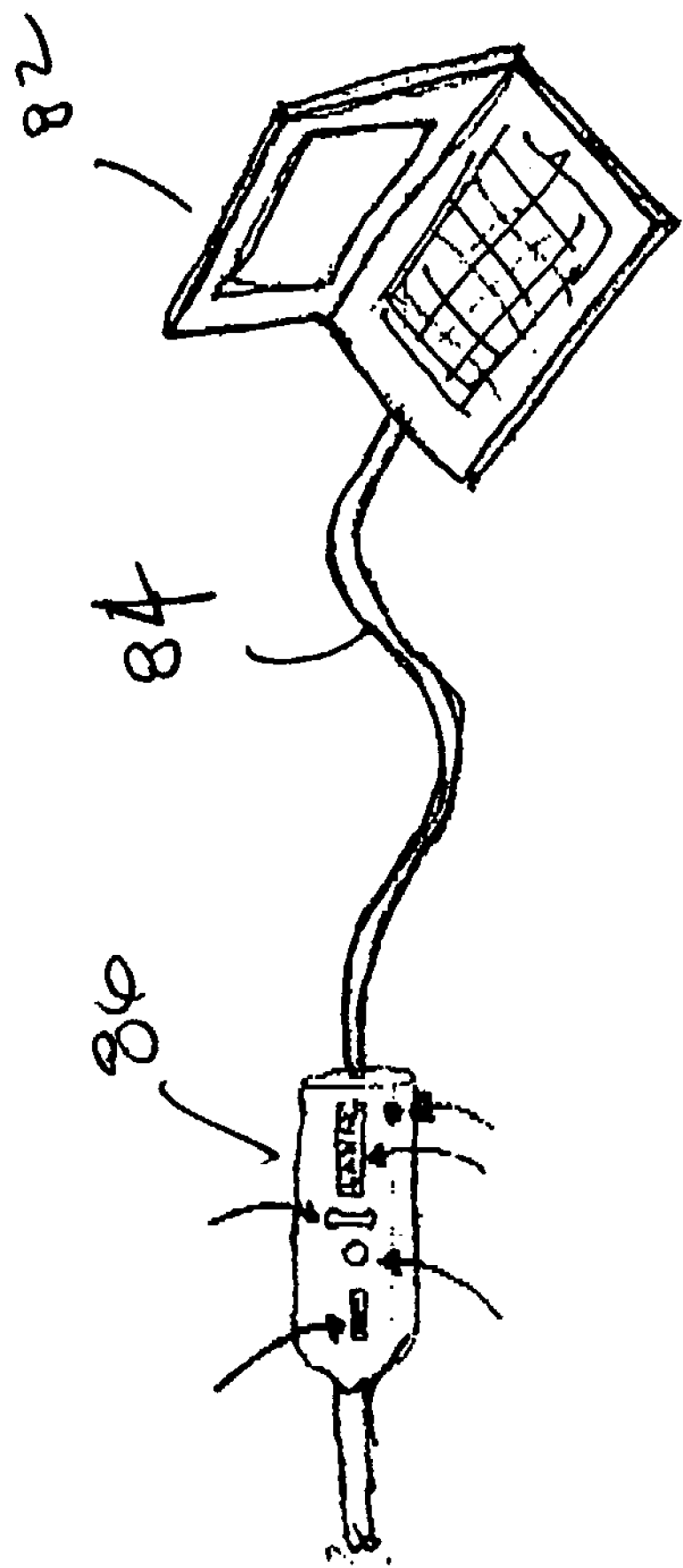
FIG. 26 is a perspective view of a computer that may be coupled to an optical imaging assembly of an apparatus, such as that shown in FIGS. 1A–1C.

For example, as shown in FIG. 26, a computer 82 may be coupled to the device 72 (not shown, see FIG. 1A), e.g., by a cable 84. Alternatively, instead of the computer 82, other display or capture devices may be coupled to the device 72, such as a laptop computer, handheld or PDA device, a computer terminal, a LCD display, standard video monitor, and the like (not shown), to display and/or store the images acquired from the fiber bundle 64. Optionally, the computer 82 (or other capture device) may provide electrical power to the device 72, light source 70, and/or other components of the apparatus 10.

For a cable connection between the device 72 and the computer 82, various protocols may be used, such as USB, Firewire, standard video signal protocols, and the like. Alternatively, the computer 82 may be coupled to the device 72 via a wireless connection, for example, including one or more transmitters and/or receiving using radio frequency signals, Bluetooth, infrared links, and the like.

In addition, the computer 82 may run software modules to enable capture, viewing, and/or manipulation of images obtained by the optical imaging assembly 62. The cable 84, the handle 30 (not shown, see FIG. 1A), or other component of the apparatus 10 may include interface features 86, such as buttons, toggles, scroll bars, dials, and the like, to facilitate interfacing with software running on the computer 82. Functions that may be performed using the interface 86 may include launching image acquisition software on the computer 82, initiating or terminating image capture, initiating still frame capture, reviewing or displaying captured images, etc. The handle 30 or other component of the apparatus 10 may also contain feedback features, e.g., one or more LEDs or LCDs, to provide feedback from software on the computer 82, e.g., related to the status of connection(s) between the computer 82 and the apparatus 10, the power status of the apparatus 10, the function of the apparatus 10, and the like.

Optionally, the apparatus 10 may include additional data acquisition features, such as a microphone (not shown), e.g., allowing procedure notes to be dictated during an imaging procedure or allowing the apparatus 10 and/or computer 10 to be controlled by voice commands. In addition or alternatively, drivers and/or software may be stored on a memory chip (not shown) in the apparatus 10 that may be uploaded to the computer 82 when connected to the apparatus 10. When a complex interface is used to connect the apparatus 10 to the computer 82 or other display device, the apparatus 10 and/or the computer 82 may be capable of disabling the complex interface and enable simple video output.

Turning to FIGS. 6–10, another preferred embodiment of an apparatus 410 is shown for visualizing and/or cannulating a body lumen. Similar to the previous embodiments, the apparatus 410 generally includes a catheter 412, a balloon 450 carried by the catheter 412, and an imaging assembly 462 for imaging through the balloon 450.

Also, similar to the previous embodiments, the catheter 412 may be an elongate tubular body including a proximal end 414, a distal end 416, and a central longitudinal axis 418 extending therebetween. The catheter 412 may be substantially flexible, semi-rigid, and/or rigid along its length, and may be formed from a variety of materials, including plastic, metal, and/or composite materials. The catheter 412 may have a diameter between about five and ten French (1.67–3.33 mm), and preferably between about six and eight French (2.00–2.67 mm).

The catheter 412 may include one or more lumens 420 also extending between the proximal and distal ends 414, 416, e.g., a cannulation lumen 420a, an inflation lumen 420b, and one or more lumens 420c–f for the imaging assembly 462 and/or one or more pullwires or other steering elements 422. In addition, the catheter 412 may include a handle (not shown) and/or other components, e.g., sources of fluid, a light source, an image capture device, and the like (also not shown) on the proximal end 414, similar to the other embodiments described herein.

Preferably, the catheter 412 includes multiple extrusions that are attached to one another to provide a desired length. For example, the catheter 412 may include a proximal portion 412a having a first cross-section, shown in FIGS. 8A and 8B, and a distal portion 412b having a second cross-section, shown in FIG. 8C. The proximal portion 412a may have a length between about nine and thirty six inches (22–90 cm), and preferably between about eighteen and twenty eight inches (45–70 cm).

The proximal portion 412a preferably includes three lumens, a cannulation lumen 420a, an inflation lumen 420b, and an accessories lumen 420c. The cannulation lumen 420a may provide a path for a guidewire or other instrument, fluid, and the like to pass between the proximal and distal ends 414, 416 of the catheter 412. Optionally, a tube 424, e.g., made from polyamide and the like, may be provided within the cannulation lumen 420a, e.g., to reinforce the cannulation lumen 420a and/or catheter 412. The inflation lumen 420b may communicate with an interior 460 of the balloon 450, similar to the previous embodiments, for delivering substantially transparent inflation media into the balloon 450. The accessories lumen 420c may carry a plurality of components, e.g., an optical imaging (fiber optic) bundle 464, pull-wire 422, and/or a set of light guides 468, similar to the previous embodiments described above.

With reference to FIGS. 7A and 8C, the distal portion 412b may have a length between about 25.4–101.6 millimeters (mm), and preferably between about 50.8–76.2 millimeters (mm). The distal portion 412b may be substantially permanently attached to the proximal portion 412a, e.g., using a lap or butt joint, and/or an adhesive, interference fit, heating, and/or sonic welding. The distal portion 412b may include continuations of the cannulation lumen 420a and inflation lumen 420b from the proximal portion 412a. In addition, the distal portion 412b may include a light guide lumen 420d, a fiber optic lumen 420e, and a pullwire lumen 420f that may communicate with the accessories lumen 420c when the proximal and distal portions 412a, 412b are attached to one another.

Preferably, the fiber optic lumen 420e is located as far away from the cannulation lumen 420a as possible in order to maximize a field of view of the fiber bundle 464 received therein. For example, as shown in FIG. 8C, the distal portion 412b may include a ridge 421 extending axially along an outer surface of the distal portion 412b, thereby maximizing a distance that the fiber optic lumen 420e may be disposed away from the cannulation lumen 420a. When the fiber bundle 464 is inserted into the catheter 412, the fiber bundle 464 may be received in the fiber optic lumen 420e in the distal portion 412b, and in the accessories lumen 420c in the proximal portion 412a. The fiber bundle 464 may be secured at one or more locations within the lumens 420e, 420c, e.g., using an adhesive and the like. Thus, the location of the fiber bundle 464 may be fixed in the distal portion 412b to stabilize its field of view relative to the catheter 412.

The pullwire lumen 420f may also be located as far away from the central axis 418, e.g., due to another ridge extending the outer surface. This arrangement may maximize a bending force applied to the catheter 412 when the pullwire 422 is pulled proximally.

Turning to FIGS. 7B and 9A–9C, the set of light guides 468 may be received in the accessories lumen 420c in the proximal portion 412a and in the light guide lumen 420d in the distal portion 412b. The set of light guides 468 may include between about one and twenty five, and preferably between about four and ten, elongate light guides. Each of the light guides 468 may be formed from a substantially transparent acrylic fiber or other light transmitting material, e.g., having a diameter between about twenty five micrometers and one millimeter (25 µm–1 mm), and preferable between about two hundred fifty and five hundred micrometers (250–500 µm).

At the proximal end 414 of the catheter 412, the light guides 468 may be substantially cylindrical, while towards the distal end 416 of the catheter 412, the light guides 468 may be tapered and/or flattened. For example, the light guides 468 may taper within a few inches of the proximal end 414 of the catheter 412, preferably reducing an overall cross-section of the light guides 468 by as much as fifty percent (50%). The light guides 468 may be disposed loosely within the accessories lumen 420c of the proximal portion 412a.

The enlarged size of the light guides 468 at the proximal end 414 of the catheter 412 may facilitate connecting the light guides 468 to a light source (not shown), as will be appreciated by those skilled in the art. Optionally, exposed lengths (not shown) of the light guides 468 beyond the proximal end 414 of the catheter 412 may be further enlarged to facilitate such connections. For example, if the light guides 468 are acrylic fibers, heat may be applied, e.g., up to one hundred seventy degrees Fahrenheit (170° F.), to cause the light guides 468 to shorten. The acrylic material may increase in diameter as it shortens, thereby increasing the diameter of the light guides 468 by as much as three times as they shorten. This may allow the light guides 468 to be columnated and connected to a light source without requiring a lens (not shown).

As the light guides 468 transition from the proximal portion 412a to the distal portion 412b, they may be linearly aligned and/or secured to each other, e.g., using an epoxy or other adhesive, and/or by reflowing the fiber material, such that surfaces of adjacent fibers are bonded at adjacent contact points. To align the light guides 468 in a desired orientation within the distal portion 412b, the light guides 468 may be received in an axial ridge or slot 423 within the distal portion 412b, as shown in FIG. 8C.

The bonded array of light guides 468 may provide a hinge, i.e., biasing the distal portion 412b of the catheter 412 to bend in a predetermined direction. Specifically, the light guides 468 may provide a higher bending moment along a bond axis "x" (shown in FIG. 9C), while exhibiting a much lower bending moment along an axis orthogonal to the bond axis "x." As the pullwire 422 is pulled proximally, the force may be transferred to the distal portion 412b of the catheter 412. Because of the asymmetric bending moments created by the light guides 468, the distal portion 412b of the catheter 412 may bend in one plane orthogonal to the bond axis "x," i.e., towards the pullwire 422, while resisting bending along the bond axis "x." This may cause the catheter 412 to curve from a location where the pullwire 422 transitions from being located at the center of the catheter 412 (e.g., as shown in FIG. 8A) to a location on the distal end 416 where the pull wire 422 is fixed (e.g., as shown in FIG. 8C).

Turning to FIGS. 10–11B, a bundle 464 of optical fibers may be provided, similar to the embodiments described above. Preferably, a lens 466 is coupled to the fiber bundle 464, e.g., a GRIN or self-oc lens, as described above. For example, as shown in FIGS. 11A and 11B, a sleeve 467, e.g., shrink wrap and the like, may be provided that may be secured around the lens 466 and the optical imaging bundle 464. Optionally, a fluid or other material (not shown) may be provided between the lens 466 and the optical imaging bundle 464 to minimize losses and/or reflection at the transition, as is known to those skilled in the art.

Figure 6:
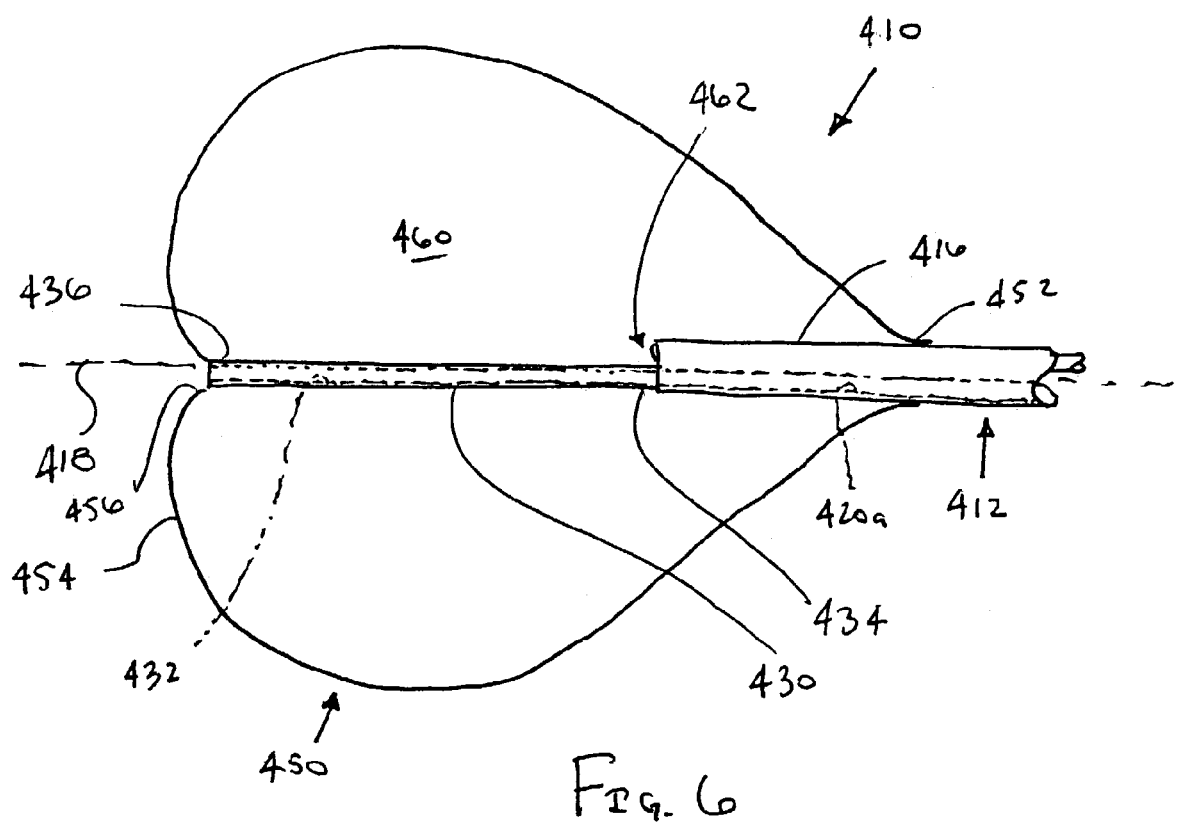
FIG. 6 is a cross-sectional side view of a distal end of another embodiment of an apparatus for cannulating a body lumen, in accordance with the present invention.

Turning to FIG. 10 with continued reference to FIG. 6, a tubular extension 430 may extend from the distal end 416 of the catheter 412. The tubular extension 430 may include a lumen 432 extending between proximal and distal ends 434, 436 of the tubular extension 430. Preferably, the tubular extension 430 has a substantially smaller diameter or other cross-section than the distal end 416 of the catheter 412.

The proximal end 434 of the tubular extension 430 may be attached to the distal end 416 of the catheter 412 such that it is coextensive with the cannulation lumen 420a. Thus, an instrument or fluid introduced through the cannulation lumen 420a may pass freely through the lumen 432 of the tubular extension 430. In addition, attaching the tubular extension 430 eccentrically to the catheter 412 opposite the optical imaging bundle 464 may minimize the extent that the tubular extension 430 obstructs the field of view of the optical imaging bundle 464.

In one embodiment, the proximal end 434 of the tubular extension 430 may be at least partially received in the cannulation lumen 420a or in a recess (not shown) concentric with the cannulation lumen 420a. Alternatively, the proximal end 434 of the tubular extension 430 may be butted against the distal end 416 of the catheter 412. In addition or alternatively, the tubular extension 4430 may be bonded to the catheter 412, e.g., using an adhesive, heating, sonic welding, and the like.

The balloon 450 may include a proximal end 452 attached to the distal end 416 of the catheter 412 and a distal end 456 attached to the distal end of the tubular extension 430. The proximal end 452 of the balloon 450 may be secured to the outer surface of the catheter 412, e.g., using an adhesive, heating, an interference fit, an outer collar (not shown), and the like, similar to the other embodiments described herein.

Turning to FIG. 14, the distal end 456 of the balloon 450 may be attached to the distal end 436 of the tubular extension 430 such that the balloon 450 at least partially inverts on itself. This may facilitate close contact between the balloon 450 and a tissue surface being viewed (not shown), which may reduce optical distortion and/or facilitate clearing fluid from between the balloon 450 and the contacted tissue surface. In addition, this arrangement may prevent the distal end 436 of the tubular extension 430 from extending substantially beyond the distal surface 454 of the balloon 450.

Similar to the previous embodiments, the balloon 450 may be expandable from a contracted condition, as shown in FIG. 12A, to an enlarged condition, as shown in FIGS. 6 and 12B–12D. In the enlarged condition, the balloon 450 may define a substantially flat distal surface 454 that may facilitate imaging tissue structures beyond the balloon 450 with the optical imaging bundle 464. Optionally, the balloon 450 may include a reflective coating (not shown) on an inside surface thereof, e.g., the proximal surface(s) opposite the distal surface 454, e.g., to concentrate light towards the distal surface 454 that may otherwise reflect or pass proximally through the balloon 450.

Turning to FIGS. 12A–13D, a method is shown for cannulating a body lumen communicating with a body cavity, e.g., a coronary sinus ostium 90 extending from a right atrium 92. Although the apparatus 410 shown is similar to that shown in FIGS. 6–10, other embodiments described herein may be used to complete similar methods. Initially, as shown in FIG. 12A, the apparatus 410 may be provided with the balloon 450 in the contracted condition. If the balloon 450 is formed from noncompliant and/or inflexible material, the balloon 450 may be folded, twisted, or otherwise compressed into the contracted condition. With the balloon collapsed, the fiber optic imaging bundle 464 may provide an unfocused image, as shown in FIG. 13A.

The distal end 416 of the apparatus 410 may be introduced into a patient's body using conventional methods used for delivering catheters or other instruments. For example, the apparatus 410 may be introduced percutaneously into the patient's vasculature from a peripheral vein, such as the femoral vein. The apparatus 410 may be advanced endoluminally, e.g., into the vena cava (not shown) and into the right atrium 92 of the heart. Optionally, the apparatus 410 may be carried within a sheath, catheter, or other delivery device (not shown) that may protect the balloon 450 or otherwise facilitate advancing the apparatus 410 through the patient's vasculature.

Once located within the right atrium 92, the balloon 450 may be expanded, as shown in FIGS. 6 and 12B (e.g., after deploying at least the distal end 416 from any delivery device). The apparatus 410 may then be manipulated to place the distal surface 454 of the balloon 450 into contact with the wall 94 of the heart within the right atrium 92, as shown in FIG. 12B. Optionally, this manipulation may involve steering the distal end 416 of the apparatus 450, e.g., using one or more pullwires or other steering mechanisms actuated from the proximal end (not shown) of the apparatus 410.

In addition or alternatively, other imaging systems may be used to monitor the apparatus 410 to facilitate accessing the coronary sinus 90. For example, external imaging systems, such as fluoroscopy, ultrasound, magnetic resonance imaging (MRI), and the like, may provide feedback as to the location and/or relative position of the distal end 416 of the apparatus 412. The distal end 416 may include markers, e.g., radiopaque bands and the like (not shown), that may facilitate such imaging. External imaging may ensure that the apparatus 410 is generally oriented towards the coronary sinus ostium 90 before optical images are acquired and the apparatus 410 is manipulated more precisely.

With the distal surface 454 of balloon 450 placed against the wall 94 of the heart, the fiber bundle 464 may be activated to image the wall 94. Sufficient distal force may be applied to the apparatus 410 to squeeze blood or other fluid from between the distal surface 454 and the wall 94, thereby clearing the field and facilitating imaging the wall 94 optionally, a substantially transparent fluid, e.g., saline, may be delivered through the catheter 412 and the tubular extension 430 to further direct blood or other fluid away from the distal surface 454 of the balloon 450 or otherwise clear the field of view of the fiber bundle 464.

Using the fiber bundle 464 to image the wall 94, the apparatus 410 may be moved along the wall 94 until a target structure is within the field of view. For example, as shown in 13B, the coronary sinus ostium 90 may be seen entering the field of view, as the balloon 450 approaches the coronary sinus ostium 90, as shown in FIG. 12B. The apparatus 410 may be moved further, as shown in FIG. 12C, until the coronary sinus ostium 90 is centered in the field of view, as shown in FIG. 13C. Preferably, the center of the field of view corresponds to the central axis 418 of the apparatus 410, e.g., aligning the tubular extension 430 with the coronary sinus ostium 90.

Once the coronary sinus ostium 90 is aligned with the tubular balloon 450 may be partially deflated, as shown in FIG. 12D, and the tubular extension 430 may be advanced at least partially into the coronary sinus 90. Thus, the tubular extension 430 may stabilize the apparatus 410 relative to the coronary sinus 90. One or more instruments, e.g., a guidewire (not shown), may be advanced into the coronary sinus 90 to access one or more coronary veins (also not shown) via the coronary sinus 90. Alternatively, the balloon 450 may be fully deflated, and the tubular extension 430 may be advanced into the coronary sinus 90 to guide the distal end 416 of the apparatus 410 into the coronary sinus 90 and/or into the coronary veins.

In one embodiment, a guidewire may provide a rail over which other instruments may be advanced into the coronary veins. For example, before or after the guidewire has been placed within a target coronary vein, the apparatus 410 may be removed from the right atrium 92 and/or completely from the patient's body. A catheter or sheath (not shown) may be advanced over the guidewire to access the coronary vein and/or to perform a procedure there. For example, with the catheter or sheath placed within the target coronary vein, the guidewire may be removed, and an electrical lead, e.g., a pacing lead for a pacemaker (also not shown), may be advanced into the coronary vein for implantation.

In one embodiment, an expandable sheath (not shown) may be delivered via the tubular extension 430 into the coronary veins, e.g., to deliver a pacing lead. Exemplary sheath apparatus and methods are disclosed in co-pending application Ser. No. 10/423,321, filed Apr. 24, 2003, the disclosure of which is expressly incorporated by reference herein. In another embodiment, the apparatus 410 may be used to deliver fluids or other materials into the coronary sinus 90. For example, a radiopaque fluid may be retroperfused into the coronary sinus 90, e.g., for obtaining a venogram of one or more coronary veins within the heart.

Turning to FIG. 15, yet another embodiment of an apparatus 510 is shown for visualizing and/or cannulating a body lumen, e.g., a coronary sinus ostium 90, similar to the previous embodiment. Similar to the embodiment shown in FIGS. 6–10, the apparatus 510 generally includes a catheter 512, a balloon 550 carried by the catheter 512, and an imaging assembly 562 for imaging through the balloon 550. The catheter 512 may be an elongate tubular body including a proximal end (not shown), a distal end 516, and a central longitudinal axis 518 extending therebetween.

The catheter 512 may include one or more lumens 520 also extending between the proximal and distal ends 514, 516, e.g., a cannulation lumen 520a, an inflation lumen (not shown), and one or more lumens (also not shown) for the imaging assembly 562 and/or one or more pullwires or other steering elements (also not shown). A tubular extension 530 may extend from the distal end 516 of the catheter 512, including a lumen 532 extending between proximal and distal ends 534, 536 of the tubular extension 430 that preferably communicates with the cannulation lumen 520a.

Similar to the previous embodiments, the balloon 550 may be expandable from a contracted condition (not shown) to an enlarged condition, shown in FIG. 15. In the enlarged condition, the balloon 550 may define a substantially flat distal surface 554 that may facilitate imaging tissue structures beyond the balloon 550 with the imaging assembly 562.

Unlike the previous embodiment, at least part of the imaging assembly 562 may be provided on an arm 568 that is extendable from the distal end 516 of the catheter 512. For example, a fiber optic imaging bundle 564 may be carried by the arm 568, while one or more light guides (not shown) may be provided on the distal end 516 of the catheter 512, similar to the apparatus 410 shown in FIGS. 6–10. Alternatively, one or more light guides (not shown) may be carried by the arm 568, in addition or instead of the fiber bundle 564.

A lens and/or prism 566 may also be carried by the arm 568 for focusing and/or redirecting the field of view of the fiber bundle 564. Preferably, a lens and prism 566 may be provided for centering the field of view towards a location where the central axis 518 intersects the distal surface 554 of the balloon 550. In addition or alternatively, the arm 568 may be bent to orient the fiber bundle 564 in a desired direction.

The arm 568 may be movable from a retracted profile (not shown), wherein the arm 568 lies close to or against the distal end 516 of the catheter 512, and an extended profile, shown in FIG. 15, wherein the arm 568 extends laterally away from the distal end 516 of the catheter 512. In one embodiment, the arm 568 may be biased to the extended profile, and may be restrained in the retracted profile, e.g., by the balloon 550 when the balloon 550 is deflated to the contracted condition. Alternatively, the arm 568 may be movable freely relative to the catheter 512, and a tether (not shown) may be connected to the arm 568 that is also connected to the balloon 550. Thus, as the balloon 550 expands, the tether may pull the arm 568 radially outwardly to the extended profile. In yet another alternative, the arm 568 may be extended and/or retracted using an actuator (not shown) operable from the proximal end of the apparatus 510.

The apparatus 510 may be used in methods similar to the apparatus 410 shown in FIGS. 6–10. One advantage of the apparatus 510 is that it may maximize the field of view of the fiber bundle 564, as compared to the apparatus 410. For example, as shown in FIG. 16A, the apparatus 410 (shown in FIGS. 6–10) may include an fiber optic imaging bundle 464 that is carried by the catheter 412 opposite a tubular extension 430. Because the tubular extension 430 extends distally into the field of view "F" of the fiber bundle 464, a blind spot $BS_1$ is created. Because the fiber bundle 464 is disposed as far away as possible from the tubular segment 430 on the catheter 410, the blind spot $BS_1$ is minimized compared to moving the fiber bundle and tubular extension closer to one another (not shown), as will be appreciated by those skilled in the art.

Turning to FIG. 16B, a field of view "F" of the apparatus 510 of FIG. 15 is shown, which has a similar diameter compared to the apparatus 410, assuming comparably sized fiber bundles 464, 564. Because the fiber bundle 564 is carried by the arm 568 (see FIG. 15), it is offset radially away from the tubular extension 530, thereby reducing a blind spot $BS_2$ as compared to the blind spot $BS_1$ shown in FIG. 16A. Thus, the arrangement of the fiber bundle 564 of the apparatus 510 of FIG. 15 may maximize the field of view, thereby reducing the risk of tissue structures passing through the blind spot undetected.

Turning to FIGS. 17A–17F, another embodiment of an apparatus 610 is shown that includes a catheter 612, a balloon 650 carried by the catheter 612, and an imaging assembly 662 for imaging through the balloon 650. The apparatus 610 differs from the previous apparatus 510 shown in FIG. 15, including a pair of fiber optic imaging bundles 664 carried by arms 668. The arms 668 may be extendable from a retracted profile, e.g., as shown in FIG. 17A to an extended profile, as shown in FIGS. 17C–17F.

In addition, the balloon 650 may be formed from an elastomeric material, such as silicone, latex, isoprene, and chronoprene, such that the balloon 650 may expand outwardly in proportion to the amount of fluid delivered into an interior 660 of the balloon 650. Preferably, the balloon 650 is attached to a tubular extension 630 extending from the distal end 616 of the catheter 612 such that, as the balloon 650 expands, a distal surface 654 of the balloon 650 may become substantially flat and/or at least partially evert, as shown in FIGS. 17E and 17F. This expanded configuration may facilitate increased contact between the distal surface 654 and a tissue structure (not shown) to be imaged.

As the balloon 650 expands, it may allow the arms 668 to expand radially outwardly to the extended profile. In addition, the arms 668 may be bent such that the fiber bundle 664 is oriented substantially distally, as shown in FIGS. 17B–17F. One or more light guides 666 may be provided on the distal end 616 of the catheter 612, similar to the previous embodiments for providing light to illuminate the distal surface 654 of the balloon 650 and beyond. Optionally, one or more electrodes 617 may be provided on the distal end 616 of the catheter, e.g., for measuring electrical potential and/or to serve as radiopaque markers to facilitate imaging the apparatus 610.

The apparatus 610 may be delivered into a body cavity, e.g., a right atrium, similar to the previous embodiments for imaging a body lumen, e.g., a coronary sinus ostium not shown). The pair of fiber bundles 664 may increase a field of view of the apparatus 610, possibly eliminating any blind spots created by the tubular extension 630, as compared to the apparatus 510 described above and including a single offset fiber bundle 564.

Figure 18A:
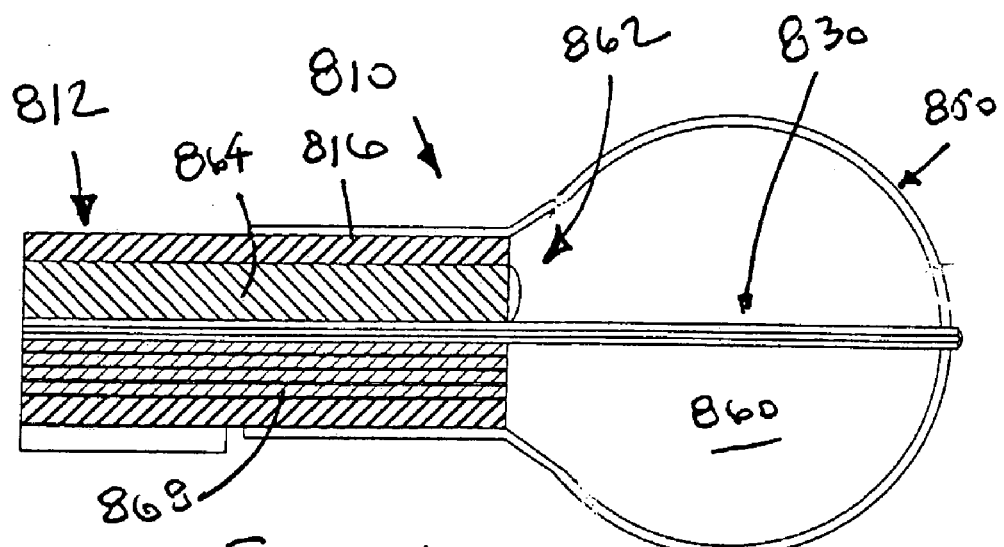
FIGS. 18A and 18B are cross-sectional side views of yet another embodiment of an apparatus for cannulating a body lumen, in accordance with the present invention.
Figure 18B:
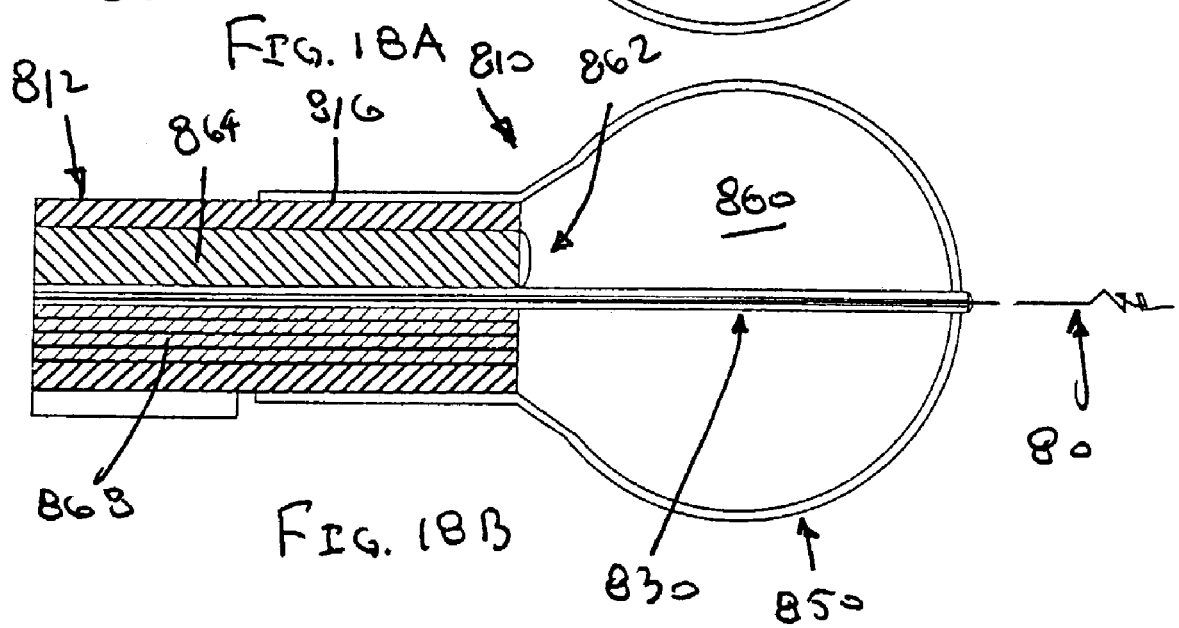

Turning to FIGS. 18A and 18B, an alternative embodiment of an apparatus 810 is shown that includes a catheter 812, a balloon 850 carried on a distal end 516 of the catheter 812, and an imaging assembly 862 for imaging through the balloon 850. The balloon 850 may be expandable between contracted and enlarged conditions, similar to other embodiments described elsewhere herein. The apparatus 810 may include one or more additional or different components or features (not shown) described elsewhere herein, similar to the other embodiments.

In addition, the apparatus 810 may include an elongate tubular member 830 extending from a proximal end (not shown) of the catheter 812 to the distal end 816, and through an interior 860 of the balloon 850. The tubular member 830 may include a lumen 832 extending therethrough through which an instrument, e.g., a guidewire 80, and/or a fluid (not shown) may be delivered to a location distally beyond the balloon 850. The tubular member 830 may be substantially flexible, but is preferably semi-rigid or substantially rigid.

The apparatus 810 may be used to deliver one or more instruments or fluids into a body lumen, similar to the other embodiments described herein. In one embodiment, the tubular member 830 is fixed relative to the catheter 512. In another embodiment, similar to that described below, the tubular member 830 may be slidable axially, i.e., distally and/or proximally, relative to the catheter 512 for changing a shape of the balloon 850 during a procedure.

Turning to FIGS. 19A and 19B, another embodiment of an apparatus 710 for cannulating a body lumen, such as a coronary sinus ostium 90, is shown. Similar to the previous embodiments, the apparatus 710 may include a catheter 712, a balloon 750 carried by the catheter 712, and an imaging assembly (not shown for simplicity) for imaging through the balloon 750.

In addition, the apparatus 710 may include an elongate cannulation member 730 that is slidably received in a lumen 720a of the catheter 712. The cannulation member 730 may be an elongate tubular body, including a lumen 832 extending between a proximal end (not shown) and a distal end 836 of the cannulation member 730. The cannulation member 730 may be substantially flexible, semi-rigid, and/or rigid, similar to the catheters described above.

The balloon 750 may be expandable between a contracted condition (not shown), and an enlarged condition, shown in FIGS. 19A and 19B. In the enlarged condition, the balloon 750 may assume a frustoconical shape. In addition, the balloon 750 may include a convex distal surface 754 or a substantially flat distal surface (not shown) in the enlarged condition. The balloon 750 may include a channel section 756 that may be attached to the cannulation member 730, e.g., adjacent its distal end 736. The channel section 756 may at least partially evert into an interior 760 of the balloon 750, as shown in FIG. 19A, and/or may extend beyond the distal surface 754 of the balloon 750, depending upon the axial position of the cannulation member 730.

During use, the cannulation member 730 may be provided initially retracted such that the channel section 756 of the balloon 750 everts into the interior 760 of the balloon 750., as shown in FIG. 19A. With the balloon 750 collapsed in the contracted condition, the apparatus 710 may be introduced into a patient's body, e.g., until the distal end 716 is located within a right atrium 92 of the patient's heart, similar to the previous embodiments. The balloon 750 may be expanded, e.g., by delivering a substantially transparent fluid into the interior 760 until the balloon 750 assumes the enlarged condition, as shown in FIG. 19A.

The distal surface 754 of the balloon 750 may be placed against the wall 94 of the heart, and manipulated while imaging through the distal surface 754 with the imaging assembly. Preferably, the distal end 836 of the cannulation member 730 may remain flush or proximal to the distal surface 754, thereby allowing the wall 94 to be imaged through the balloon 750. A more proximal position may prevent the cannulation member 730 from interfering substantially with a field of view of the imaging assembly, which may facilitate aligning the apparatus 710 with the coronary sinus ostium 90.

When the apparatus 710 is aligned with the coronary sinus ostium 90, as shown in FIG. 19B, the cannulation member 730 may be advanced distally into the coronary sinus 90. Optionally, the balloon 750 may be at least partially deflated as or after the cannulation member 730 is advanced, thereby allowing the distal end 716 of the catheter 712 to be inserted into the coronary sinus 90 as well.

An instrument, e.g., a guidewire, catheter, and the like (not shown), may be delivered through the lumen 732 of the cannulation member 730, e.g., to perform a diagnostic and/or therapeutic procedure within a region accessed, e.g., within a coronary vein (not shown). Once the procedure(s) is(are) completed, the apparatus 710 may be removed from the patient's body.

Turning to FIGS. 20A–20C, still another embodiment of an apparatus 910 is shown for visualizing and/or cannulating a body lumen (not shown). Similarly to the previous embodiments, the apparatus 910 may include a catheter 912, a balloon 950 carried by a distal end 916 of the catheter 912, and an imaging assembly 962, similar to the previous embodiments.

Unlike the previous embodiments, the balloon 950 may not include a channel extending therethrough, and instead includes an interior 960 that is substantially enclosed. A lumen, e.g., an inflation lumen 920b, may extend from a proximal end (not shown) of the catheter 912 to the distal end 916 that communicates with the interior 960 of the balloon 950. In addition, the catheter 912 may include a cannulation lumen 920a that may extend along an outer surface of the catheter 912 through which an instrument, e.g., guidewire 80, and/or a fluid may be delivered to the distal end 916 of the catheter 912 outside the balloon 950.

The apparatus 910 may also include an elongate member 930 that is slidable within the inflation lumen 920b or optionally through another lumen (not shown) that communicates with the interior 960 of the balloon 950. Preferably, the elongate member 930 includes a substantially blunt distal end 936 that may be advanced into the interior 960 of the balloon 950. For example, the elongate member 930 may be inserted into the inflation lumen 920b from the proximal end of the catheter 912, or the elongate member 930 may not be removable from the catheter 912, and, instead, may be slidable in a limited range within the inflation lumen 920b.

During use, the apparatus 910 may be advanced into a patient's body, e.g., into a right atrium of a heart or other body cavity (not shown) with the balloon 950 collapsed, similar to the previous embodiments. Within the body cavity, the balloon 950 may be expanded, as shown in FIG. 20A, such that the balloon 950 defines a substantially flat distal surface 954. The distal surface 954 may be placed against a wall of the body cavity, and manipulated, e.g., steered and/or otherwise moved, until a target body lumen, e.g., a coronary sinus ostium (not shown) enters the field of view of a fiber optic imaging bundle 964 of the imaging assembly 962, similar to the previous embodiments.

Once the target body lumen is located and the apparatus 910 is aligned with the body lumen, the elongate member 930 may be advanced through the inflation lumen 920b and into the interior 960 of the balloon 950. The distal end 936 of the elongate member 930 may contact the distal surface 954 of the balloon 950, whereupon, further distal movement of the elongate member 930 may cause the balloon 950 to change shape, as shown in FIGS. 20B and 20C. Because of the substantially blunt shape of the distal end 936 of the elongate member, the balloon 950 may be changed without substantial risk of puncturing or otherwise damaging the balloon 950.

For example, the elongate member 930 may be advanced to elongate the balloon 950 and/or reduce a diameter or other cross-section of the balloon 950. This may at least partially introduce the balloon 950 into the body lumen, e.g., the coronary sinus, thereby stabilizing the apparatus 910 relative to the body lumen. Alternatively, the elongate member 930 may reduce a cross-section of the balloon 950, thereby allowing an instrument, e.g., a guidewire 80, to be advanced through the cannulation lumen 920a and past the balloon 950 without substantial risk of puncturing or otherwise damaging the balloon 950. The guidewire 80 may be advanced into the body lumen, whereby additional instruments (not shown) may be advanced over the guidewire 80 into the body lumen, as described above.

Alternatively, as shown in FIGS. 21A–21C, an apparatus 1010 may be provided that includes a balloon 1050 carried by a catheter 1012, and an imaging assembly 1062 for imaging through the balloon 1050. Similar to the previous embodiments, substantially transparent fluid, e.g., saline, may be introduced into the balloon 1050 to expand the balloon 1050 and allow a distal surface 1054 to be placed into contact with tissue structures, e.g., a wall of a heart, similar to the previous embodiments.

An elongate member, e.g., a guidewire 1030, may be inserted through an inflation lumen 1020b of the catheter 912 into the interior of the balloon 1050, e.g., after the balloon 950 has been inflated and/or used to identify and/or locate a body lumen (not shown), similar to the previous embodiment. As shown in FIG. 21B, the guidewire 1030 may be advanced until a distal end 1036 of the guidewire 1030 punctures the balloon 1050 and passes therethrough into the target body lumen. Optionally, the distal end 1032 of the guidewire 1030 may be sharpened or otherwise adapted to facilitate puncturing the balloon 1050.

As the inflation fluid escapes through the puncture created in the balloon 1050, the balloon 1050 may collapse, as shown in FIG. 21C. The guidewire 1030 may be advanced into the body lumen, and one or more instruments (not shown) may be advanced over the guidewire, e.g., after removing the apparatus 1010, as described above.

Figure 22A:
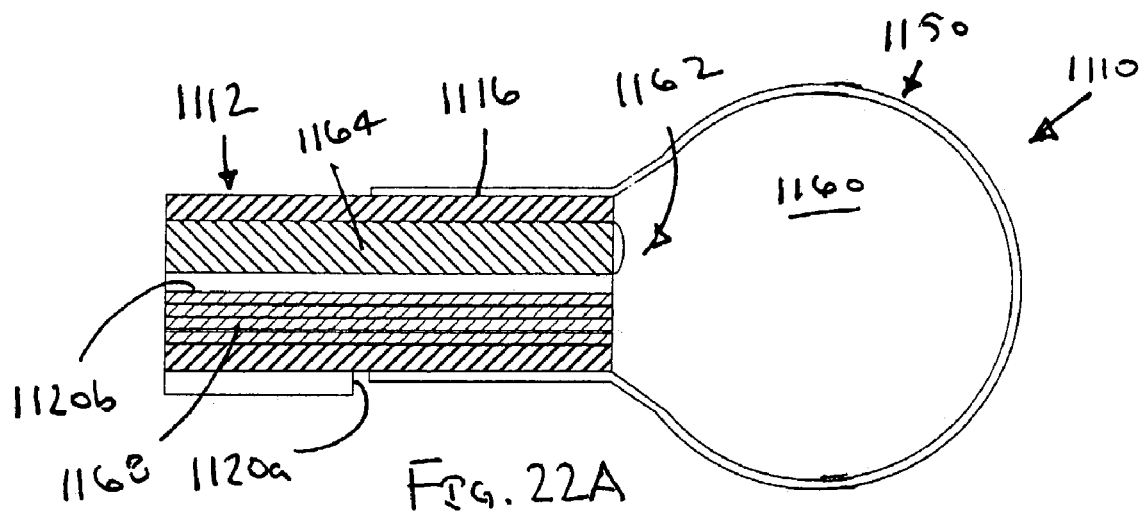
FIGS. 22A–22C are cross-sectional side views of yet another embodiment of an apparatus for cannulating a body lumen, in accordance with the present invention.
Figure 22B:
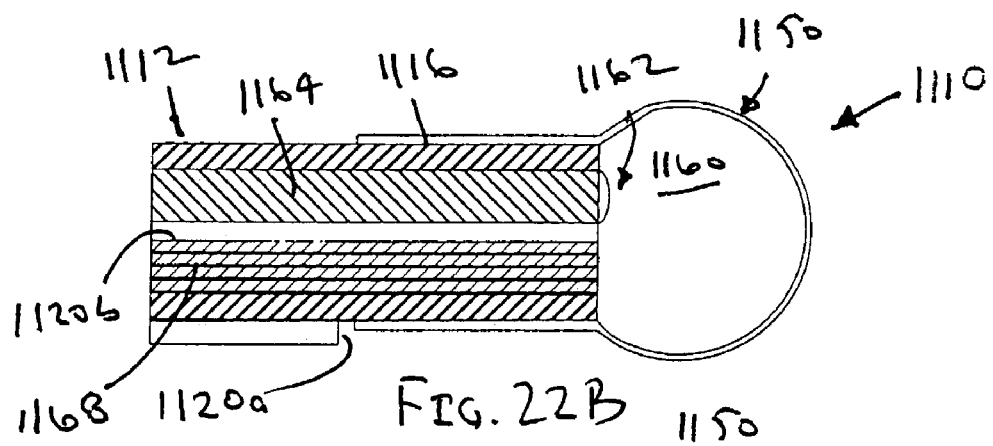
Figure 22C:
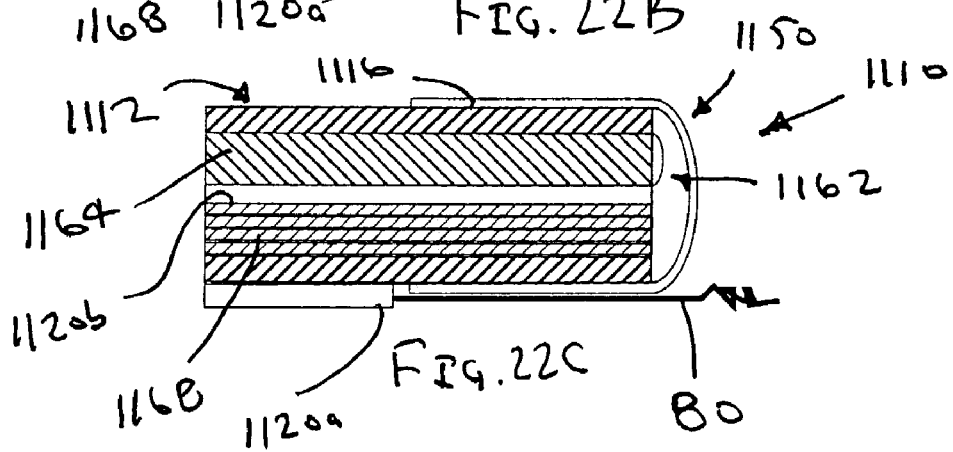

In a further alternative, shown in FIGS. 22A–22C, an apparatus 1110 may be provided that includes a catheter 1112, a balloon 1150 carried on a distal end 1116 of the catheter 1112, and an imaging assembly 1162 for imaging through the balloon 1150. Similar to the previous embodiment, an inflation lumen 120b extends through the catheter 1112 to communicate with an interior 1160 of the balloon 1150. Unlike the previous embodiment, a cannulation lumen 1120a extends along an outer surface of the catheter 1112.

During use, as shown in FIG. 22A, the apparatus 1110 may be introduced into a body cavity (not shown), whereupon the balloon 1150 may be expanded and contacted with a wall of the body cavity for imaging tissue structures therethrough. When the apparatus 1110 is aligned with a body lumen extending from the body cavity, the balloon 1150 may be at least partially deflated, as shown in FIGS. 22B and 22C. Once the cannulation lumen 1120a is not obstructed by the balloon 1150, a guidewire 80 or other instrument may be advanced through the cannulation lumen 1120a past the balloon 1150, and preferably into the body lumen, similar to the procedures described above.

Turning to FIGS. 23A–25B, yet another embodiment of an apparatus 1210 is shown for visualizing and/or cannulating a body lumen, e.g., a coronary sinus ostium extending from a right atrium of a heart (not shown). Similar to the previous embodiments, the apparatus 1210 includes a catheter 1212 carrying an imaging assembly 1262 on its distal end 1216, which may include a fiber optic imaging bundle 1264 and one or more light guides 1268, as described above.

In addition, the apparatus 1210 may include a solid bulb 1250 carried on the distal end 1216 of the catheter 1212. The bulb 1250 may be formed from a substantially rigid or semi-rigid material that is substantially transparent, e.g., acrylic, polycarbonate, polymethlymethacrylate (PMMA), and nylon. The bulb 1250 may define an interior 1260 that may be filled with substantially transparent fluid, e.g., saline, to facilitate imaging through the bulb 1250 using the imaging assembly 1262.

In the embodiment shown in FIGS. 23A and 24A, the fiber optic imaging bundle 1264 and the light guide 1268 may be disposed side-by-side when viewed from the end of the catheter 1212, as best seen in FIG. 24A. In addition, similar to any of the embodiments described herein, the apparatus 1210 may include one or more pullwires, e.g., the two pullwires 1222 shown, for steering the catheter 1212, as described above.

Alternatively, as shown in FIGS. 23B and 24B, the apparatus 1210' may include a centrally disposed fiber optic imaging bundle 1264,' a plurality of light guides 1268' may be disposed around the imaging bundle 1264,' and one or more pullwires 1222.'

With reference to FIGS. 23A and 24A, during use, the apparatus 1210 may be introduced into a body cavity (not shown), and the bulb 1250 may be placed against a wall of the body cavity to image the wall through the bulb 1250 using the imaging assembly 1262. Preferably, sufficient distal force is applied to clear blood or other fluid from between the bulb 1250 and the wall of the body cavity. Optionally, an external cannulation lumen (not shown) may be provided on the catheter 1250 for delivering a guidewire or other instrument (not shown) into a body lumen (also not shown) communicating with the body cavity, as described above. The alternative embodiment shown in FIGS. 23B and 24B may be used in a substantially similar manner.

In another alternative, shown in FIGS. 25A and 25B, an apparatus 1210" may be provided that includes a substantially transparent bulb 1250" and an imaging assembly 1262," similar to the previous embodiment. In addition, an occlusion member, e.g., a compliant balloon 1230" may be provided on the catheter 1212" proximal to the bulb 1250."

The catheter 1212" may include multiple lumens, e.g., an inflation lumen 1220b" and a perfusion lumen 1220c" that extend from a proximal end to the distal end 1216" of the catheter 1212." The inflation lumen 1220b" may communicate with an interior 1232" of the occlusion balloon 1230" for inflating and/or deflating the balloon 1230." The perfusion lumen 1220c" may communicate with an outlet port 1225" for delivering fluids from a proximal end of the catheter 1212" to a location distal to the occlusion balloon 1230."

During use, the apparatus 1210" may be introduced into a body cavity, e.g., a right atrium of a heart (not shown), similar to the embodiments described above, with the occlusion balloon 1230" collapsed. The bulb 1250" may be pressed against a wall of the heart in order to image and locate the coronary sinus ostium (not shown), also similar to the previous embodiments. Once the coronary sinus ostium is located, the apparatus 1210" may be inserted into the coronary sinus until the occlusion balloon 1230" is at least partially received in the coronary sinus.

The occlusion balloon 1230" may then be inflated to engage the wall of the coronary sinus, preferably substantially sealing the coronary sinus from fluid flow therethrough. Fluid may be delivered through the perfusion lumen 1220c" until it exits the port 1225" and enters the coronary sinus, thereby perfusing the coronary sinus in a retrograde direction. The fluid may include a diagnostic agent, e.g., contrast for performing a venogram or other procedure, and/or a therapeutic agent. Upon completing the procedure, the occlusion balloon 1230" may be deflated, and the apparatus 1210" may be removed from the patient's heart and/or body.

Turning to FIGS. 27A–27D, another embodiment of an apparatus 1310 is shown for cannulating a coronary sinus ostium or other body lumen of a patient (not shown). Generally, the apparatus 1310 includes a catheter 1312, including a proximal end 1314, a distal end 1316, and a longitudinal axis 1318 extending therebetween. In addition, the catheter 1312 may include one or more lumens, e.g., a cannulation lumen 1320, which may extend along an outer surface of the catheter 1312, as shown, or may be located within the catheter 1312 (not shown). In addition, the catheter 1312 may include one or more pullwires or other steering elements (no shown) that may be controlled from a handle 1330, similar to the previous embodiments.

A plurality of oxygen sensors 1350 may be carried on the distal end 1316 of the catheter 1312. Preferably, the oxygen sensors 1350 are disposed on the ends of wires or other elongate filaments 1352 that are biased away from one another, e.g., to provide an annular array of oxygen sensors. The filaments 1352 may extend through the catheter 1312 from the distal end 1316 to the proximal end 1314. Alternatively, the oxygen sensors 1350 may be provided on an exterior of a balloon or other expandable member (not shown) carried on the distal end 1316 of the catheter 1312.

Preferably, as shown in FIG. 27D, each filament 1352 includes one or more electrical leads 1354, 1356, and one or more stiffening members 1358. The stiffening members 1358 may bias the oxygen sensors 1350 to the radial configuration shown. The electrical leads 1354, 1356 may be coupled to a capture device 1360, shown in FIG. 27A, which may include a power source, a controller, memory, or other components (not shown) for operating and/or receiving data from the oxygen sensors 1350. The capture device 1360 may analyze and/or otherwise capture oxygen measurements from the oxygen sensors 1350.

During use, the apparatus 1310 may be introduced into a right atrium or other body cavity (not shown), similar to the previous embodiments. Preferably, the oxygen sensors 1350 are constrained close to one another during advancement, e.g., to protect the oxygen sensors 1350 and/or to minimize a profile of the apparatus 1310. For example, the apparatus 1310 may be provided within a sheath, catheter, or other delivery device (not shown) that may facilitate advancing the apparatus 1310 through the patient's vasculature.

Once the distal end 1316 is located within the right atrium, the oxygen sensors 1350 may be deployed from the delivery device. Because blood flowing from the coronary sinus ostium has less oxygen than blood flowing through the right atrium, the oxygen sensors 1350 may be used to locate the coronary sinus ostium. Once the coronary sinus ostium is located, the apparatus 1310 may be advanced into the coronary sinus, or a guidewire or other instrument (not shown) may be advanced from the apparatus 1310, e.g., from the cannulation lumen 1320 into the coronary sinus, similar to the previous embodiments. Thus, the guidewire may provide a rail for advancing other instruments into the coronary sinus and/or into coronary veins accessed therethrough.

In an alternative embodiment, shown in FIGS. 28A and 28B, an apparatus 1410 may be provided that includes a catheter 1412 carrying one or more oxygen sensors 1450 and a balloon or other occlusion member 1430. In the preferred embodiment shown, a single oxygen sensor 1450 may be provided on the distal end 1416 of the catheter 1412, and one or more electrical leads 1454, 1456 may extend from the oxygen sensor 1450 through the catheter 1412, e.g., to a capture device (not shown), similar to the previous embodiment. The balloon 1430 may facilitate retrograde perfusion of the coronary sinus, similar to the embodiment shown in FIG. 25A and described above. Instead of using a fiber optic imaging bundle, the oxygen sensor, preferably a solid-state device, may facilitate monitoring perfusion of the coronary sinus or other body lumen.

Turning to FIGS. 29A–29C, another embodiment of an apparatus 1510 is shown that may include a catheter 1512, a balloon 1550, and an imaging assembly (not shown for simplicity) carried by the catheter 1510, similar to the embodiments described above. In addition, the apparatus 1510 may include an elongate member 1530 that may be deployed from a channel 1552 extending through the balloon 1550. The elongate member 1530 may be slidable relative to the catheter 1512, e.g., such that a distal end 1536 of the elongate member 1530 may be advanced through the channel 1552 and beyond a distal surface 1554 of the balloon 1550, as shown in FIG. 29B.

The apparatus 1510 may include a handle and/or one or more controls (not shown), e.g., at a proximal end (also not shown) of the catheter 1512, e.g., for sliding the elongate member 1530 relative to the catheter 1512. For example, a tab, bar, or other element (not shown) coupled to the elongate member 1530 may be slidable in a slot in a handle for limiting movement of the elongate member 1530.

The elongate member 1530 may facilitate cannulating a coronary sinus ostium 90 or other body lumen, and/or may facilitate localizing other morphological features of tissue being imaged, e.g., to maintain a position of the distal end 1516 of the catheter 1512 relatively constant. Thus, the elongate member 1530 may act as a stabilization member or a localization member, e.g., allowing the balloon 1550 to be deflated, as shown in FIG. 29C, without moving the distal end 1516 of the catheter 1512 laterally away from the ostium 90 or other morphological feature. In addition or alternatively, the elongate member 1530 may facilitate advancing the apparatus 1510 into the ostium 90 or other lumen, e.g., after the balloon 1550 has been deflated, also as shown in FIG. 29C.

The distal end 1536 of the elongate member 1530 may be constructed for a particular purpose, e.g., having a size for cannulating an ostium of a particular size and/or having a substantially atruamatic tip. Optionally, the distal end 1536 may be shapeable and/or steerable, using an internal pullwire or other element, similar to the catheter embodiments described above. Alternatively, the elongate member 1530 may be adapted for stabilizing the distal end 1516 of the catheter 1512 using other morphologic features of tissue being imaged.

For example, as shown in FIG. 30A, the distal end 1536' may have a cone or wedge shape that may allow the distal end 1536' to be wedged or otherwise inserted temporarily into a crevasse or depression (not shown), e.g., in a chamber of a heart, such as the trebaculae carne on a wall of a heart. Alternatively, as shown in FIG. 30B, an elongate member 1530" may be provided that includes a bent distal end 1536," e.g., having an "S" or other curved shape. In a further alternative, shown in FIG. 30C, an elongate member 1530''' is shown that includes a forked distal end 1536''' that may be used to straddle a ridge, such as the eustation ridge in the right atrium (not shown).

Returning to FIGS. 29A–29C, preferably, the elongate member 1530 is movable between a retracted position, such as that shown in FIG. 29A, and a deployed position, as shown in FIG. 29B. The retracted position may allow substantial apposition of the distal surface 1554 of the balloon 1550 against a structure being imaged, e.g., a wall 94 of a heart, e.g., to facilitate imaging the structure, similar to the embodiments described previously. When the elongate member 1530 is moved towards the deployed position, as shown in FIG. 29B, the distal end 1536 may interact with the structure of interest.

For example, as shown in FIG. 29B, the distal end 1536 may at least partially enter the coronary sinus ostium 90 to temporarily localize the distal end 1516 of the catheter 1512 at the coronary sinus ostium 90. During use, the apparatus 1510 may be introduced into the right atrium 92 of a heart, similar to the previous embodiments, and then the balloon 1550 may expanded and pressed against the wall 94 of the heart. The wall 94 may be imaged through the distal surface 1554, and the distal end 1512 manipulated until the coronary sinus ostium 90 is aligned with the channel 1552.

As shown in FIG. 29B, the distal end 1536 of the elongate member 1503 may be deployed until at least partially received in the coronary sinus ostium 90, thereby localizing and/or stabilizing the catheter 1512. As shown in FIG. 29C, the balloon 1550 may be at least partially deflated, whereupon the distal end 1516 of the catheter 1512 may be inserted into the coronary sinus ostium 90, thereby cannulating the ostium 90.

Although different embodiments have been described herein with particularity as including specific components and/or features, it will be appreciated that each of the embodiments described above may include components and/or features specifically described with respect to individual embodiments. For example, any of the embodiments described above may include one or more of the following: a handle on a proximal end of a catheter, one or more pullwires or other steering elements for steering a catheter and/or a localization/stabilization member, steering controls or actuator, a source of light, a capture device, e.g., including a display, processor for analyzing image data, and/or memory for storing imaging data, sources of fluid, e.g., for delivering inflation media, diagnostic, and/or therapeutic agents, and the like. Thus, different components may be provided on each of the embodiments, depending upon a specific application.

In addition, each of the apparatus described may be used to perform any of the procedures described herein and should not limited to the specific examples described. For example, any of the apparatus described may be used for imaging, accessing, and/or cannulating a collapsible lumen, such as the colon. Embodiments with channels through balloons or other expandable and/or displacement members may be used to deliver insufflation media, e.g., carbon dioxide, nitrogen, and/or air, into a collapsible lumen to facilitate performing a procedure therein.

While the invention is susceptible to various modifications, and alternative forms, specific examples thereof have been shown in the drawings and described herein in detail. It should be understood, however, that the invention is not to be limited to the particular forms or methods disclosed, but, to the contrary, the invention is to cover all modifications, equivalents and alternatives falling within the scope of the appended claims.

What is claimed is:

1. An apparatus for locating morphological features within a body cavity, comprising:
 a flexible tubular member comprising a proximal end, a distal end having a size for introduction into a body cavity, and defining a longitudinal axis extending between the proximal and distal ends;

an optical imaging assembly carried by the distal end of the tubular member for imaging beyond the distal end;
a substantially transparent displacement member carried by the distal end of the tubular member and at least partially surrounding the optical imaging assembly; and
a localization member slidably received in a cannulation lumen of the tubular member, the localization member being movable beyond the distal end of the tubular member for temporarily localizing the distal end of the tubular member at a morphologic feature within a body cavity,
wherein the displacement member comprises an expandable membrane, and wherein the localization member is coupled to distal end of the membrane, and
wherein the localization member is movable for changing a shape of the membrane when the membrane is expanded to an enlarged condition.

2. The apparatus of claim 1, wherein the expandable membrane comprises a channel communicating with the cannulation lumen, the localization member being extendable from a retracted position proximal to the surface through the channel to a deployed position beyond the surface for localizing the distal end of the tubular member.

3. The apparatus of claim 1, wherein the expandable membrane comprises a compliant balloon.

4. The apparatus of claim 1, wherein the expandable membrane comprises a noncompliant balloon.

5. The apparatus of claim 1, wherein the localization member terminates in a distal tip configured for engaging a morphological feature.

6. The apparatus of claim 5, wherein the distal tip is selected from a tapered distal tip, a forked distal tip, and a steerable distal tip.

7. An apparatus for locating morphological features within a body cavity, comprising:
a flexible tubular member comprising a proximal end, a distal end having a size for introduction into a body cavity, and defining longitudinal axis extending between the proximal and distal ends;
an optical imaging assembly carried by the distal end of the tubular member for imaging beyond the distal end;
a substantially transparent displacement member carried by the distal end of the tubular member and at least partially surrounding the optical imaging assembly; and
a localization member slidably received in a cannulation lumen of the tubular member, the localization member being movable beyond the distal end of the tubular member for temporarily localizing the distal end of the tubular member at a morphologic feature within a body cavity,
wherein the displacement member comprises an expandable member comprising an interior communicating with the cannulation lumen, and wherein the localization member comprises a distal tip that is advanceable into the interior of the expandable member to puncture through the expandable member.

8. The apparatus of claim 1, further comprising a capture device coupled to the proximal end of the tubular member and coupled to the optical imaging assembly for acquiring images obtained using the optical imaging assembly.

9. The apparatus of claim 8, wherein the capture device comprises at least one of a display, a processor for processing the acquired images, and memory for storing the acquired images.

10. An apparatus for locating morphological features within a body cavity, comprising:
a flexible tubular member comprising a proximal end, a distal end having a size for introduction into a body cavity, and defining a longitudinal axis extending between the proximal and distal ends;
an optical imaging assembly carried by the distal end of the tubular member for imaging beyond the distal end;
a substantially transparent displacement member carried by the distal end of the tubular member and at least partially surrounding the optical imaging assembly; and
a localization member slidably received in a cannulation lumen of the tubular member, the localization member being movable beyond the distal end of the tubular member for temporarily localizing the distal end of the tubular member at a morphologic feature within a body cavity,
wherein the displacement member comprises an expandable membrane, and wherein the localization member is coupled to a distal end of the membrane, and
wherein the localization member is movable between a retracted position wherein the distal end of the membrane at least partially everts into an interior of the membrane, and an extended position wherein the distal end of the membrane extends distally to create a nipple.

11. An apparatus for locating morphologic features within a body cavity, comprising:
a flexible tubular member comprising a proximal end, a distal end having a size for introduction into a body cavity, and defining a longitudinal axes extending between the proximal and distal ends;
an optical imaging assembly carried by the distal end of the tubular member for imaging beyond the distal end;
a substantially transparent displacement member carried by the distal end of the tubular member and at least partially surrounding the optical imaging assembly;
a localization member slidably received in a cannulation lumen of the tubular member, the localization member being movable beyond the distal end to the tubular member for temporarily localizing the distal end of the tubular member at a morphologic feature within a body cavity; and
an occlusion member carried on the distal end of the tubular member proximal to the displacement member.

12. The apparatus of claim 11, wherein the tubular member comprises a perfusion lumen extending to an outlet port between the occlusion member and the displacement member for delivering fluid from the proximal end of the tubular member to a location distal to the occlusion member.

13. The apparatus of claim 1, wherein the distal end of the tubular member is steerable.

14. An apparatus for imaging within a body lumen, comprising:
a flexible tubular member comprising proximal and distal ends defining a longitudinal axis therebetween;
a substantially transparent expandable member on the distal end of the tubular member, the expandable member being expandable from a contracted condition to an enlarged condition when fluid is introduced through the tubular member into an interior of the expandable member; and
an optical imaging element disposed within the interior of the expandable member, the imaging element extending from the distal end of the tubular member in a direction at least partially transversely relative to the longitudinal axis.

15. The apparatus of claim 14, wherein the optical imaging element comprises a plurality of optical fibers.

16. The apparatus of claim 15, wherein the optical imaging element further comprises a lens coupled to the plurality of optical fibers for imaging through a distal end of the expandable member.

17. The apparatus of claim 16, wherein the distal end of the expandable member is substantially flat.

18. The apparatus of claim 16, wherein the distal end of the expandable member is contoured to match a surface relief of a target anatomical feature to be imaged.

19. The apparatus of claim 15, further comprising a light source carried by the distal end of the tubular member for delivering light from the interior through the expandable member.

20. The apparatus of claim 14, further comprising a channel extending through the expandable member that communicates with a lumen extending between the proximal and distal ends of the tubular member.

21. The apparatus of claim 20, further comprising a source of fluid coupled to the proximal end of the tubular member, the source of fluid communicating with the lumen for delivering fluid through the channel to a location beyond the expandable member.

22. The apparatus of claim 20, further comprising an elongate member insertable through the lumen such that a distal end of the elongate member may be extended through the channel to a location beyond the expandable member.

23. The apparatus of claim 20, wherein the lumen and channel extend substantially concentrically along a central longitudinal axis of the tubular member.

24. The apparatus of claim 20, wherein the lumen extends along a periphery of the tubular member, and wherein the channel extends along a wall of the expandable member.

25. The apparatus of claim 14, wherein the expandable member comprises a balloon.

26. The apparatus of claim 25, wherein the balloon comprises compliant material.

27. The apparatus of claim 14, wherein the tubular member comprises one or more lumens extending between the proximal and distal end for at least one of perfusing, infusing, and aspirating fluids.

28. The apparatus of claim 14, further comprising a steering member extending along at least a distal portion of the tubular member for bending the distal end transversely relative to the longitudinal axis.

29. An apparatus for accessing a body lumen communicating with a body cavity, comprising:
a flexible tubular member comprising a proximal end, a distal end having a size for introduction into a body cavity, and defining a longitudinal axis extending between the proximal and distal ends;
an inner member slidably coupled to the tubular member;
a substantially transparent expandable member comprising a proximal end attached to the distal end of the tubular member and a distal end attached to a distal end of the inner member, the expandable member being expandable from a contracted condition to an enlarged condition when fluid is introduced through the tubular member into an interior of the expandable member, the inner member being slidable from a retracted position wherein the distal end of the expandable member at least partially everts into the interior of the expandable member and an extended position wherein the expandable member defines a stabilizing element insertable into a body lumen extending from a body cavity for stabilizing the tubular member relative to the body lumen; and
an optical imaging element carried by the distal end of the tubular member for imaging through the expandable member.

30. The apparatus of claim 29, wherein a distal portion of the expandable member tapers when the inner member is directed to the extended position.

31. The apparatus of claim 29, further comprising a steering member extending along at least a distal portion of the tubular member for bending the distal end transversely relative to the longitudinal axis.

32. The apparatus of claim 29, wherein the expandable member comprises a balloon.

33. The apparatus of claim 30, wherein the balloon comprises compliant material.

34. A method for cannulating a body lumen communicating with a body cavity of a patient, the method comprising:
inserting a distal end of a tubular member into the body cavity, the tubular member comprising a substantially transparent expandable member thereon in a contracted condition;
expanding the expandable member within the body cavity;
placing a surface of the expanded expandable member in contact with a wall of the body cavity in order to image the wall through the expandable member;
manipulating the tubular member to move the expandable member along the wall, while imaging the wall through the expandable member, until the body lumen is identified; and
advancing an instrument from the tubular member into the body lumen.

35. The method of claim 34, wherein the body cavity comprises a right atrium of a patient's heart, and wherein the body lumen comprises a coronary sinus ostium.

36. The method of claim 35, wherein the tubular member is advanced from a peripheral vein through a vena cava to insert the distal end into the right atrium.

37. The method of claim 34, wherein the instrument comprises at least one of a guide wire, a cannula, and a catheter.

38. The method of claim 34, wherein the instrument is advanced into the body lumen through a channel extending through the expandable member that communicates with the lumen.

39. The method of claim 38, wherein the channel is disposed concentrically with a central axis of the tubular member, and wherein the tubular member is manipulated to align the channel with the body lumen.

40. The method of claim 34, wherein the surface of the expanded expandable member is placed in contact with the wall of the body cavity with sufficient force to at least partially clear fluid from between the surface and the wall to enhance imaging the wall.

41. The method of claim 34, further comprising delivering a fluid between the surface and the wall to at least partially clear bodily fluid from between the surface and the wall to enhance imaging the wall.

42. The method of claim 34, further comprising expanding an occlusion member on the tubular member to substantially seal the body lumen from the body cavity.

43. The method of claim 42, further comprising infusing fluid into the body lumen.

44. The method of claim 43, wherein the fluid comprises contrast, and wherein the method further comprises obtaining a venogram of a location distal to the occlusion member.

45. The method of claim 42, further comprising aspirating fluid from the body lumen.

46. A apparatus for accession a body lumen communicating with a body cavity, comprising:
- a flexible tubular member comprising a proximal end, a distal end sized for introduction into a body cavity, and a central longitudinal axis extending between the proximal and distal ends;
- a tubular extension attached eccentrically to the distal end and extending distally from the distal end substantially parallel to the longitudinal axis;
- a substantially transparent expandable member comprising a proximal end attached to the distal end of the tubular member and a distal end attached to the tubular extension, the expandable member being expandable from a contracted condition to an enlarged condition when fluid is introduced through the tubular member into an interior of the expandable member; and
- an optical imaging element carried by the distal end of the tubular member for imaging through the expandable member.

47. The apparatus of claim 46, wherein the optical imaging element is disposed away from the central longitudinal axis to minimize obstruction of a field of view of the optical imaging element by the tubular extension.

48. The apparatus of claim 47, wherein the optical imaging element is carried by an arm that is extendable away from the distal end.

49. The apparatus of claim 47, wherein the optical imaging element is fixed to the distal end generally opposite the tubular extension.

50. The apparatus of claim 46, wherein the tubular member comprises a cannulation lumen extending between the proximal and distal ends, the cannulation lumen communication with the tubular extension for delivering an instrument through the tubular extension into a body lumen.

51. The apparatus of claim 46, wherein the expandable member comprises a substantially flat distal surface in the enlarged condition to facilitate imaging tissue structures beyond the expandable member with the optical imaging element.

52. The apparatus of claim 46, wherein the distal end of the tubular member is steerable.

53. The apparatus of claim 46, wherein the optical imaging element comprises a plurality of optical fibers.

54. The apparatus of claim 53, wherein the optical imaging element further comprises a lens coupled to the plurality of optical fibers for imaging through the expandable member.

55. The apparatus of claim 46, further comprising a light source carried by the distal end of the tubular member for delivering light through the expandable member.

56. The apparatus of claim 55, wherein the light source comprises a plurality of optical fibers disposed away from the central longitudinal axis.

57. The apparatus of claim 56, wherein the plurality of optical fibers are linearly aligned with one another.

* * * * *